United States Patent
Neumann

(10) Patent No.: US 11,901,056 B2
(45) Date of Patent: Feb. 13, 2024

(54) METHODS AND SYSTEMS FOR INFORMED SELECTION OF PRESCRIPTIVE THERAPIES

(71) Applicant: KPN Innovations, LLC, Lakewood, CO (US)

(72) Inventor: Kenneth Neumann, Lakewood, CO (US)

(73) Assignee: KPN Innovations, LLC

( * ) Notice: Subject to any disclaimer, the term of this patent is extended or adjusted under 35 U.S.C. 154(b) by 857 days.

(21) Appl. No.: 16/911,921

(22) Filed: Jun. 25, 2020

(65) Prior Publication Data

US 2021/0166797 A1 Jun. 3, 2021

Related U.S. Application Data

(63) Continuation-in-part of application No. 16/699,617, filed on Nov. 30, 2019, now Pat. No. 10,734,105.

(51) Int. Cl.
| | | |
|---|---|---|
| *G16H 20/00* | (2018.01) | |
| *G16H 20/10* | (2018.01) | |
| *G16H 10/60* | (2018.01) | |
| *G06N 20/00* | (2019.01) | |

(52) U.S. Cl.
CPC ............ *G16H 20/10* (2018.01); *G06N 20/00* (2019.01); *G16H 10/60* (2018.01)

(58) Field of Classification Search
CPC ...... G16H 20/00; G16H 10/60; G06K 9/6276; G06K 9/6223; G06N 20/00; G06N 3/08
See application file for complete search history.

(56) References Cited

U.S. PATENT DOCUMENTS

| | | |
|---|---|---|
| 10,282,512 B2 | 5/2019 | Bennett et al. |
| 2018/0137941 A1 | 5/2018 | Chen |
| 2018/0271455 A1 | 9/2018 | Zhong et al. |
| 2018/0365383 A1 | 12/2018 | Bates |
| 2019/0189259 A1 | 6/2019 | Clark |

(Continued)

FOREIGN PATENT DOCUMENTS

WO WO-2020002478 A1 * 1/2020 ............. G06N 20/00

OTHER PUBLICATIONS

MacLean, Elizabeth; Cisar, Laura; Mehle, Kimberly; Eremina, Daria; Quigley, Jane M. "Real-World Axitinib Use in the United States: A Retrospective Study Using Linked Datasets." Journal of managed care & specialty pharmacy 22.6: 723-732u. (Jun. 2016) (Year: 2016).*

(Continued)

*Primary Examiner* — Linh Giang Le
(74) *Attorney, Agent, or Firm* — Caldwell Intellectual Property Law

(57) ABSTRACT

A system for informed selection of prescriptive therapies. The system includes a computing device configured to receive compositional training data containing a plurality of unclassified data entries. The system is configured to retrieve a user biological profile and generate an unsupervised machine-learning model that utilizes a biological profile as an input and outputs a therapy response label. The system selects a therapy response model and receives from a remote device a proposed prescriptive therapy. The system creates a therapy response model and identifies a prescriptive therapy label for a proposed prescriptive therapy.

20 Claims, 9 Drawing Sheets

(56) References Cited

U.S. PATENT DOCUMENTS

| | | |
|---|---|---|
| 2019/0221311 A1* | 7/2019 | Takeuchi ................. G06N 3/02 |
| 2019/0244712 A1 | 8/2019 | Barbieri et al. |
| 2019/0326002 A1 | 10/2019 | Mould |
| 2019/0333623 A1 | 10/2019 | Hibbard |
| 2019/0341153 A1 | 11/2019 | Ng et al. |
| 2020/0051679 A1* | 2/2020 | Bostic .................... G16H 10/60 |
| 2021/0158956 A1* | 5/2021 | Rodziewicz ........... G16H 20/90 |

OTHER PUBLICATIONS

"Learning Doctors' Medicine Prescription Pattern for Chronic Disease Treatment by Mining Electronic Health Records:A Multi-Task Learning Approach"; Apr. 16, 2018; NCBI; https://www.ncbi.nim.nih.gov/pmc/articles/PMC5977645/.

* cited by examiner

| Genetic Feature | Constitutional Feature | Ecological Feature |
|---|---|---|
| Absorption | Absorption | Alcohol use |
| Distribution | Distribution | Climate |
| Metabolism | Metabolism | Culture |
| Excretion | Excretion | Educational status |
| Body weight | Age | Language |
| Genetic conditions | Alcohol use | Socioeconomic factors |
| Genetic polymorphism of drug metabolizing enzymes | Body weight | Profession |
| Height | Cardiovascular function | Diet |
| Race | Diet | Diseases |
| Receptor sensitivity | Diseases | Co-morbid conditions |
| Sex | Co-morbid conditions | Drug adherence |
| | Height | Medical practices |
| | Kidney function | Pollution |
| | Liver function | Smoking |
| | Receptor sensitivity | Stress |
| | Smoking | Sunlight exposure |
| | Stress | Therapeutic approach |

*FIG. 4*

METHODS AND SYSTEMS FOR INFORMED SELECTION OF PRESCRIPTIVE THERAPIES

CROSS-REFERENCE TO RELATED APPLICATIONS

This continuation-in-part application claims the benefit of priority of U.S. Non-Provisional patent application Ser. No. 16/699,617, filed on Nov. 30, 2019 and entitled "METHODS AND SYSTEMS FOR INFORMED SELECTION OF PRESCRIPTIVE THERAPIES", which is incorporated by reference herein in its entirety.

FIELD OF THE INVENTION

The present invention generally relates to the field of artificial intelligence. In particular, the present invention is directed to methods and systems for informed selection of prescriptive therapies.

BACKGROUND

Accurate and proper selection of prescriptive therapies is imperative to reduce total health care spending and reduce adverse reactions that can potentially cause life threatening reactions. Currently, unreliable measures exist to predict how an individual will respond to a particular prescriptive therapy. This can be further complicated by the multitude of factors that must be considered when selecting an appropriate treatment.

SUMMARY OF THE DISCLOSURE

In an aspect, a system for informed selection of prescriptive therapies, the system comprising a computing device, the computing device configured to receive a prescriptive therapy label; identify a prescriptive therapy instruction set including a first prescriptive therapy as a function of the prescriptive therapy label where calculating further comprises generating as a function of a prescriptive machine-learning process, the prescriptive therapy instruction set, wherein the prescriptive machine-learning process is trained using prescriptive training data, wherein prescriptive training data contains a plurality of data entries containing a prescriptive therapy label element correlated with a prescriptive therapy instruction set; and identifying the prescriptive instruction set as a function of generating the prescriptive machine-learning process; and recommend a prescriptive therapy instruction set.

In an aspect, a method of informed selection of prescriptive therapies, the method comprising receiving by a computing device, a prescriptive therapy label; calculating by the computing device, a prescriptive therapy instruction set including a first prescriptive therapy as a function of the prescriptive therapy label where calculating further comprises generating as a function of a prescriptive machine-learning process, the prescriptive therapy instruction set, wherein the prescriptive machine-learning process is trained using prescriptive training data, wherein prescriptive training data contains a plurality of data entries containing a prescriptive therapy label element correlated with a prescriptive therapy instruction set; and identifying the prescriptive instruction set as a function of generating the prescriptive machine-learning process; and recommending by the computing device, a prescriptive therapy instruction set.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIG. 4 is a diagrammatic representation of unsupervised features;

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for informed selection of prescriptive therapies. In an embodiment, a computing device receives compositional training data and generates an unsupervised machine-learning model. An unsupervised machine-learning model utilizes a biological profile as an input and outputs a therapy response label. A computing device selects a therapy response model as a function of generating an unsupervised machine-learning model. In an embodiment, an unsupervised machine-learning model may include a clustering algorithm such as a k-means clustering algorithm. A computing device receives a proposed prescriptive therapy from a remote device. A computing device generates a therapy response model that relates biological profiles to prescriptive therapy labels. A computing device identifies a prescriptive therapy label for a proposed prescriptive therapy. A prescriptive therapy label may identify if a proposed prescriptive therapy is compatible or incompatible with a user's body.

Figure 1:
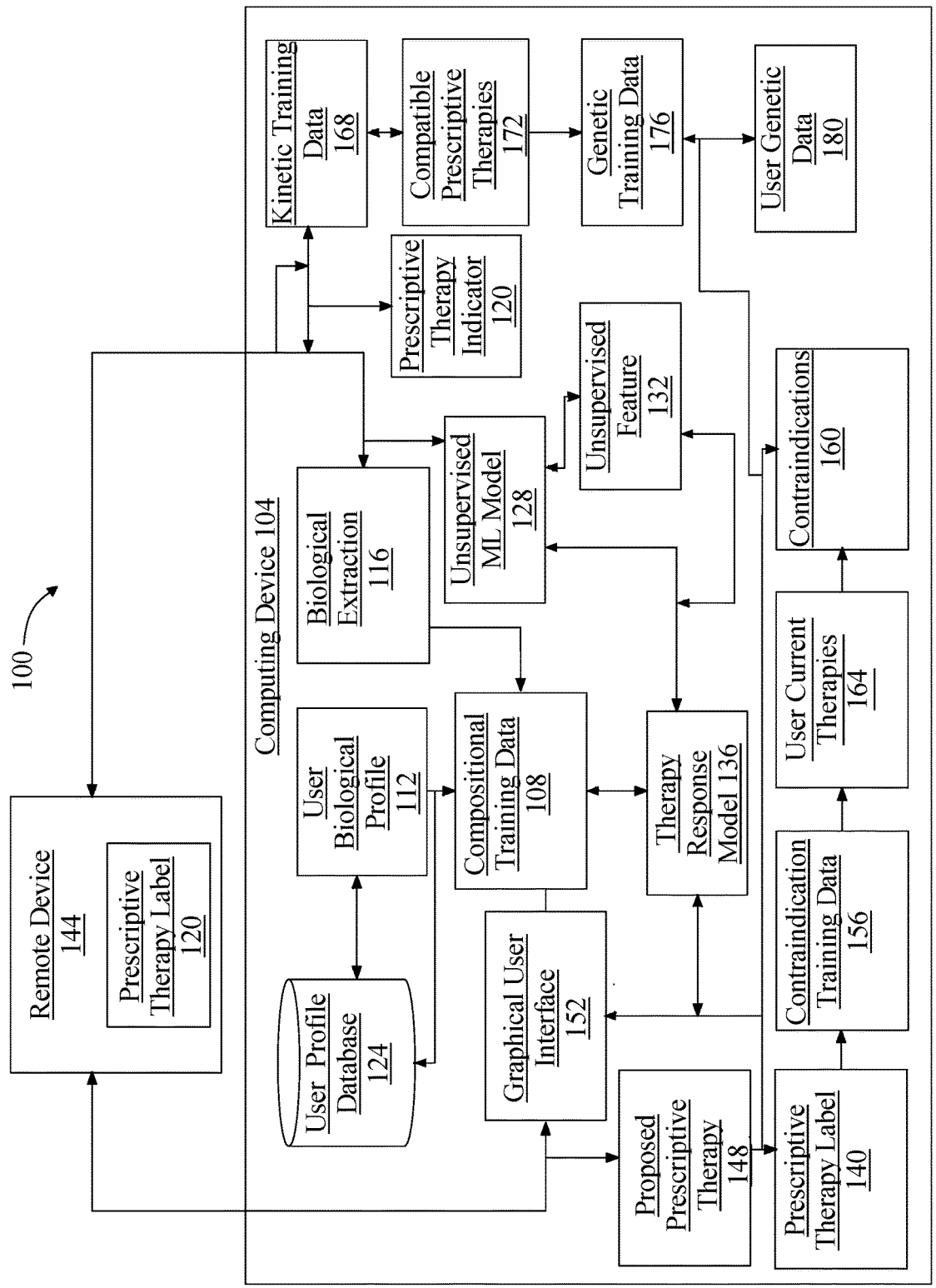
FIG. 1 is a block diagram illustrating an exemplary embodiment of a system for informed selection of prescriptive therapies.

Referring now to FIG. 1, an exemplary embodiment of a system 100 for informed selection of regulated ameliorative remedies is illustrated. System 100 includes a computing device 104. Computing device 104 may include any computing device 104 as described in this disclosure, including without limitation a microcontroller, microprocessor, digital signal processor (DSP) and/or system on a chip (SoC) as described in this disclosure. Computing device 104 may include, be included in, and/or communicate with a mobile device such as a mobile telephone or smartphone. Computing device 104 may include a single computing device 104 operating independently or may include two or more computing device 104 operating in concert, in parallel, sequentially or the like; two or more computing devices 104 may be included together in a single computing device 104 or in two or more computing devices 104. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices 104, and any combinations thereof. A network may employ a wired and/or a wireless mode of communication. In general, any network topology may be used. Information (e.g., data, software etc.) may be communicated to and/or from a computer and/or a computing device 104. Computing device 104 may include but is not limited to, for example, a computing device 104 or cluster of computing devices 104 in a first location and a second computing device 104 or cluster of computing devices 104 in a second location. Computing device 104 may include one or more computing devices 104 dedicated to data storage, security, distribution of traffic for load balancing, and the like. Computing device 104 may distribute one or more computing tasks as described below across a plurality of computing devices 104 of computing device 104, which may operate in parallel, in series, redundantly, or in any other manner used for distribution of tasks or memory between computing devices 104. Computing device 104 may be implemented using a "shared nothing" architecture in which data is cached at the worker; in an embodiment, this may enable scalability of system 100 and/or computing device 104.

Still referring to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, computing device 104 is configured to receive compositional training data 108. Compositional training data 108 includes a plurality of unclassified data entries. "Unclassified data entries" as used in this disclosure, are data entries that have not been assigned, generated, and/or calculated category labels. Classification may include a process of predicting a class of given data entries. Classification may include using predictive modeling that approximates a mapping function from input variables to discrete output variables. Classification may be performed utilizing classification algorithms that include for example decision trees, naïve Bayes, artificial neural networks, boosting, kernel methods, and/or k-nearest neighbors algorithms. Classification may involve one or more processes that generate classified data entries.

With continued reference to FIG. 1, unclassified data entries may be stored in any suitable data and/or data type. For instance and without limitation, dataset may include textual data, such as numerical, character, and/or string data. Textual data may include a standardized name and/or code for a disease, disorder, or the like; codes may include diagnostic codes and/or diagnosis codes, which may include without limitation codes used in diagnosis classification systems such as The International Statistical Classification of Diseases and Related Health Problems (ICD). In general, there is no limitation on forms textual data or non-textual data used as unclassified data entries may take; persons skilled in the art, upon reviewing the entirety of this disclosure, will be aware of various forms which may be suitable for use as dataset consistently with this disclosure.

With continued reference to FIG. 1, training data, as used in this disclosure, is data containing correlations that a machine-learning process may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine-learning processes as described in further detail below. Training data may be formatted and/or organized by categories of data elements, for instance by associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements; for instance, and without limitation, training data may be provided in fixed-length formats, formats linking positions of data to categories such as comma-separated value (CSV) formats and/or self-describing formats such as extensible markup language (XML), enabling processes or devices to detect categories of data.

Alternatively or additionally, and still referring to FIG. 1, training data may include one or more elements that are not categorized; that is, training data may not be formatted or contain descriptors for some elements of data. Machine-learning algorithms and/or other processes may sort training data according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data to be made applicable for two or more distinct machine-learning algorithms as described in further detail below. Training data used by computing device 104 may correlate any input data as described in this disclosure to any output data as described in this disclosure.

With continued reference to FIG. 1, computing device 104 is configured to retrieve a user biological profile 112. A "user biological profile" as used in this disclosure, is one or more elements of data pertaining to a user. A user biological profile 112 includes one or more biological extraction 116 and one or more prescriptive therapy indicators. A "biological extraction 116" as used in this disclosure includes at least an element of user biological data. As used in this disclosure, "biological data" is any data indicative of a person's biological state; biological state may be evaluated with regard to one or more measures of health of a person's body, one or more systems within a person's body such as a circulatory system, a digestive system, a nervous system, or the like, one or more organs within a person's body, and/or any other subdivision of a person's body useful for diagnostic or prognostic purposes. For instance, and without limitation, a particular set of biomarkers, test results, and/or biochemical information may be recognized in a given medical field as useful for identifying various disease conditions or prognoses within a relevant field. As a non-limiting example, and without limitation, biological data describing red blood cells, such as red blood cell count, hemoglobin levels, hematocrit, mean corpuscular volume, mean corpuscular hemoglobin, and/or mean corpuscular hemoglobin concentration may be recognized as useful for identifying various conditions such as dehydration, high testosterone, nutrient deficiencies, kidney dysfunction, chronic inflammation, anemia, and/or blood loss.

With continued reference to FIG. 1, biological state data may include, without limitation, hematological data, such as red blood cell count, which may include a total number of red blood cells in a person's blood and/or in a blood sample, hemoglobin levels, hematocrit representing a percentage of blood in a person and/or sample that is composed of red blood cells, mean corpuscular volume, which may be an estimate of the average red blood cell size, mean corpuscular hemoglobin, which may measure average weight of hemoglobin per red blood cell, mean corpuscular hemoglobin concentration, which may measure an average concentration of hemoglobin in red blood cells, platelet count, mean platelet volume which may measure the average size of platelets, red blood cell distribution width, which measures variation in red blood cell size, absolute neutrophils, which measures the number of neutrophil white blood cells, absolute quantities of lymphocytes such as B-cells, T-cells, Natural Killer Cells, and the like, absolute numbers of monocytes including macrophage precursors, absolute numbers of eosinophils, and/or absolute counts of basophils. Biological state data may include, without limitation, immune function data such as Interleukine-6 (IL-6), TNF-alpha, systemic inflammatory cytokines, and the like.

Continuing to refer to FIG. 1, biological state data may include, without limitation, data describing blood-born lipids, including total cholesterol levels, high-density lipoprotein (HDL) cholesterol levels, low-density lipoprotein (LDL) cholesterol levels, very low-density lipoprotein (VLDL) cholesterol levels, levels of triglycerides, and/or any other quantity of any blood-born lipid or lipid-containing substance. Biological state data may include measures of glucose metabolism such as fasting glucose levels and/or hemoglobin A1-C (HbA1c) levels. Biological state data may include, without limitation, one or more measures associated with endocrine function, such as without limitation, quantities of dehydroepiandrosterone (DHEAS), DHEA-Sulfate, quantities of cortisol, ratio of DHEAS to cortisol, quantities of testosterone quantities of estrogen, quantities of growth hormone (GH), insulin-like growth factor 1 (IGF-1), quantities of adipokines such as adiponectin, leptin, and/or ghrelin, quantities of somatostatin, progesterone, or the like. Biological state data may include measures of estimated glomerular filtration rate (eGFR). Biological state data may include quantities of C-reactive protein, estradiol, ferritin, folate, homocysteine, prostate-specific Ag, thyroid-stimulating hormone, vitamin D, 25 hydroxy, blood urea nitrogen, creatinine, sodium, potassium, chloride, carbon dioxide, uric acid, albumin, globulin, calcium, phosphorus, alkaline phosphatase, alanine amino transferase, aspartate amino transferase, lactate dehydrogenase (LDH), bilirubin, gamma-glutamyl transferase (GGT), iron, and/or total iron binding capacity (TIBC), or the like. Biological state data may include antinuclear antibody levels. Biological state data may include aluminum levels. Biological state data may include arsenic levels. Biological state data may include levels of fibrinogen, plasma cystatin C, and/or brain natriuretic peptide.

Continuing to refer to FIG. 1, biological state data may include measures of lung function such as forced expiratory volume, one second (FEV-1) which measures how much air can be exhaled in one second following a deep inhalation, forced vital capacity (FVC), which measures the volume of air that may be contained in the lungs. Biological state data may include a measurement blood pressure, including without limitation systolic and diastolic blood pressure. Biological state data may include a measure of waist circumference. Biological state data may include body mass index (BMI).

Biological state data may include one or more measures of bone mass and/or density such as dual-energy x-ray absorptiometry. Biological state data may include one or more measures of muscle mass. Biological state data may include one or more measures of physical capability such as without limitation measures of grip strength, evaluations of standing balance, evaluations of gait speed, pegboard tests, timed up and go tests, and/or chair rising tests.

Still viewing FIG. 1, biological state data may include one or more measures of cognitive function, including without limitation Rey auditory verbal learning test results, California verbal learning test results, NIH toolbox picture sequence memory test, Digital symbol coding evaluations, and/or Verbal fluency evaluations. Biological state data may include one or more evaluations of sensory ability, including measures of audition, vision, olfaction, gustation, vestibular function and pain.

Continuing to refer to FIG. 1, biological state data may include psychological data. Psychological data may include any data generated using psychological, neuro-psychological, and/or cognitive evaluations, as well as diagnostic screening tests, personality tests, personal compatibility tests, or the like; such data may include, without limitation, numerical score data entered by an evaluating professional and/or by a subject performing a self-test such as a computerized questionnaire. Psychological data may include textual, video, or image data describing testing, analysis, and/or conclusions entered by a medical professional such as without limitation a psychologist, psychiatrist, psychotherapist, social worker, a medical doctor, or the like. Psychological data may include data gathered from user interactions with persons, documents, and/or computing devices; for instance, user patterns of purchases, including electronic purchases, communication such as via chat-rooms or the like, any textual, image, video, and/or data produced by the subject, any textual image, video and/or other data depicting and/or describing the subject, or the like. Any psychological data and/or data used to generate psychological data may be analyzed using machine-learning and/or language processing module 136 as described in this disclosure.

Still referring to FIG. 1, biological state data may include genomic data, including deoxyribonucleic acid (DNA) samples and/or sequences, such as without limitation DNA sequences contained in one or more chromosomes in human cells. Genomic data may include, without limitation, ribonucleic acid (RNA) samples and/or sequences, such as samples and/or sequences of messenger RNA (mRNA) or the like taken from human cells. Genetic data may include telomere lengths. Genomic data may include epigenetic data including data describing one or more states of methylation of genetic material. Biological state data may include proteomic data, which as used herein is data describing all proteins produced and/or modified by an organism, colony of organisms, or system of organisms, and/or a subset thereof. Biological state data may include data concerning a microbiome of a person, which as used herein includes any data describing any microorganism and/or combination of microorganisms living on or within a person, including without limitation biomarkers, genomic data, proteomic data, and/or any other metabolic or biochemical data useful for analysis of the effect of such microorganisms on other biological state data of a person, as described in further detail below.

With continuing reference to FIG. 1, biological state data may include one or more user-entered descriptions of a person's biological state. One or more user-entered descriptions may include, without limitation, user descriptions of symptoms, which may include without limitation current or past physical, psychological, perceptual, and/or neurological symptoms, user descriptions of current or past physical, emotional, and/or psychological problems and/or concerns, user descriptions of past or current treatments, including therapies, nutritional regimens, exercise regimens, pharmaceuticals or the like, or any other user-entered data that a user may provide to a medical professional when seeking treatment and/or evaluation, and/or in response to medical intake papers, questionnaires, questions from medical professionals, or the like. Biological state data may include any biological state data, as described above, describing any multicellular organism living in or on a person including any parasitic and/or symbiotic organisms living in or on the persons; non-limiting examples may include mites, nematodes, flatworms, or the like. Examples of biological state data described in this disclosure are presented for illustrative purposes only and are not meant to be exhaustive.

With continued reference to FIG. 1, biological state data may include, without limitation any result of any medical test, biological assessment, cognitive assessment, psychological assessment, or the like. System 100 may receive at least a biological data from one or more other devices after performance; system 100 may alternatively or additionally perform one or more assessments and/or tests to obtain at least a biological data, and/or one or more portions thereof, on system 100. For instance, at least biological data may include or more entries by a user in a form or similar graphical user interface 152 object; one or more entries may include, without limitation, user responses to questions on a psychological, behavioral, personality, or cognitive test. For instance, at least a server 104 may present to user a set of assessment questions designed or intended to evaluate a current state of mind of the user, a current psychological state of the user, a personality trait of the user, or the like; at least a server 104 may provide user-entered responses to such questions directly as at least a biological data and/or may perform one or more calculations or other algorithms to derive a score or other result of an assessment as specified by one or more testing protocols, such as automated calculation of a Stanford-Binet and/or Wechsler scale for IQ testing, a personality test scoring such as a Myers-Briggs test protocol, or other assessments that may occur to persons skilled in the art upon reviewing the entirety of this disclosure. Biological state data may include any data relating to genetic data, epigenetic, user health records, patient inputs and the like.

With continued reference to FIG. 1, assessment and/or self-assessment data, and/or automated or other assessment results, obtained from a third-party device; third-party device may include, without limitation, a server or other device (not shown) that performs automated cognitive, psychological, behavioral, personality, or other assessments. Third-party device may include a device operated by an informed advisor. An informed advisor may include any medical professional who may assist and/or participate in the medical treatment of a user. An informed advisor may include a medical doctor, nurse, physician assistant, pharmacist, yoga instructor, nutritionist, spiritual healer, meditation teacher, fitness coach, health coach, life coach, and the like.

With continued reference to FIG. 1, biological data may include data describing one or more test results, including results of mobility tests, stress tests, dexterity tests, endocrinal tests, genetic tests, and/or electromyographic tests, biopsies, radiological tests, genetic tests, and/or sensory tests. Persons skilled in the art, upon reviewing the entirety of this disclosure, will be aware of various additional examples of at least a biological sample consistent with this disclosure.

With continued reference to FIG. 1, biological data may include one or more user body measurements. A "user body measurement" as used in this disclosure, includes a measurable indicator of the severity, absence, and/or presence of a disease state. A "disease state" as used in this disclosure, includes any harmful deviation from the normal structural and/or function state of a human being. A disease state may include any medical condition and may be associated with specific symptoms and signs. A disease state may be classified into different types including infectious diseases, deficiency diseases, hereditary diseases, and/or biological diseases. For instance and without limitation, internal dysfunction of the immune system may produce a variety of different diseases including immunodeficiency, hypersensitivity, allergies, and/or autoimmune disorders.

With continued reference to FIG. 1, user body measurements may be related to particular dimensions of the human body. A "dimension of the human body" as used in this disclosure, includes one or more functional body systems that are impaired by disease in a human body and/or animal body. Functional body systems may include one or more body systems recognized as attributing to root causes of disease by functional medicine practitioners and experts. A "root cause" as used in this disclosure, includes any chain of causation describing underlying reasons for a particular disease state and/or medical condition instead of focusing solely on symptomatology reversal. Root cause may include chains of causation developed by functional medicine practices that may focus on disease causation and reversal. For instance and without limitation, a medical condition such as diabetes may include a chain of causation that does not include solely impaired sugar metabolism but that also includes impaired hormone systems including insulin resistance, high cortisol, less than optimal thyroid production, and low sex hormones. Diabetes may include further chains of causation that include inflammation, poor diet, delayed food allergies, leaky gut, oxidative stress, damage to cell membranes, and dysbiosis. Dimensions of the human body may include but are not limited to epigenetics, gut-wall, microbiome, nutrients, genetics, and/or metabolism.

With continued reference to FIG. 1, epigenetic, as used herein, includes any user body measurements describing changes to a genome that do not involve corresponding changes in nucleotide sequence. Epigenetic body measurement may include data describing any heritable phenotypic. Phenotype, as used herein, include any observable trait of a user including morphology, physical form, and structure. Phenotype may include a user's biochemical and biological properties, behavior, and products of behavior. Behavioral phenotypes may include cognitive, personality, and behavior patterns. This may include effects on cellular and biological phenotypic traits that may occur due to external or environmental factors. For example, DNA methylation and histone modification may alter phenotypic expression of genes without altering underlying DNA sequence. Epigenetic body measurements may include data describing one or more states of methylation of genetic material.

With continued reference to FIG. 1, gut-wall, as used herein, includes the space surrounding the lumen of the gastrointestinal tract that is composed of four layers including the mucosa, submucosa, muscular layer, and serosa. The mucosa contains the gut epithelium that is composed of goblet cells that function to secrete mucus, which aids in lubricating the passage of food throughout the digestive tract. The goblet cells also aid in protecting the intestinal wall from destruction by digestive enzymes. The mucosa includes villi or folds of the mucosa located in the small intestine that increase the surface area of the intestine. The villi contain a lacteal, that is a vessel connected to the lymph system that aids in removal of lipids and tissue fluids. Villi may contain microvilli that increase the surface area over which absorption can take place. The large intestine lack villi and instead a flat surface containing goblet cells are present.

With continued reference to FIG. 1, gut-wall includes the submucosa, which contains nerves, blood vessels, and elastic fibers containing collagen. Elastic fibers contained within the submucosa aid in stretching the gastrointestinal tract with increased capacity while also maintaining the shape of the intestine. Gut-wall includes muscular layer which contains smooth muscle that aids in peristalsis and the movement of digested material out of and along the gut. Gut-wall includes the serosa which is composed of connective tissue and coated in mucus to prevent friction damage from the intestine rubbing against other tissue. Mesenteries are also found in the serosa and suspend the intestine in the abdominal cavity to stop it from being disturbed when a person is physically active.

With continued reference to FIG. 1, gut-wall body measurement may include data describing one or more test results including results of gut-wall function, gut-wall integrity, gut-wall strength, gut-wall absorption, gut-wall permeability, intestinal absorption, gut-wall barrier function, gut-wall absorption of bacteria, gut-wall malabsorption, gut-wall gastrointestinal imbalances and the like.

With continued reference to FIG. 1, gut-wall body measurement may include any data describing blood test results of creatinine levels, lactulose levels, zonulin levels, and mannitol levels. Gut-wall body measurement may include blood test results of specific gut-wall body measurements including d-lactate, endotoxin lipopolysaccharide (LPS) Gut-wall body measurement may include data breath tests measuring lactulose, hydrogen, methane, lactose, and the like. Gut-wall body measurement may include blood test results describing blood chemistry levels of albumin, bilirubin, complete blood count, electrolytes, minerals, sodium, potassium, calcium, glucose, blood clotting factors, With continued reference to FIG. 1, gut-wall body measurement may include one or more stool test results describing presence or absence of parasites, *firmicutes, Bacteroidetes*, absorption, inflammation, food sensitivities. Stool test results may describe presence, absence, and/or measurement of acetate, aerobic bacterial cultures, anaerobic bacterial cultures, fecal short chain fatty acids, beta-glucuronidase, cholesterol, chymotrypsin, fecal color, *cryptosporidium* EIA, *Entamoeba histolytica*, fecal lactoferrin, *Giardia lamblia* EIA, long chain fatty acids, meat fibers and vegetable fibers, mucus, occult blood, parasite identification, phospholipids, propionate, putrefactive short chain fatty acids, total fecal fat, triglycerides, yeast culture, n-butyrate, pH and the like.

With continued reference to FIG. 1, gut-wall body measurement may include one or more stool test results describing presence, absence, and/or measurement of microorganisms including bacteria, archaea, fungi, protozoa, algae, viruses, parasites, worms, and the like. Stool test results may contain species such as *Bifidobacterium* species, *campylobacter* species, *Clostridium difficile, Cryptosporidium* species, *Cyclospora cayetanensis, Cryptosporidium* EIA, *Dientamoeba fragilis, Entamoeba histolytica, Escherichia coli, Entamoeba histolytica, Giardia, H. pylori, Candida albi-* cans, *Lactobacillus* species, worms, macroscopic worms, mycology, protozoa, Shiga toxin *E. coli*, and the like.

With continued reference to FIG. 1, gut-wall body measurement may include one or more microscopic ova exam results, microscopic parasite exam results, protozoan polymerase chain reaction test results and the like. Gut-wall body measurement may include enzyme-linked immunosorbent assay (ELISA) test results describing immunoglobulin G (Ig G) food antibody results, immunoglobulin E (Ig E) food antibody results, Ig E mold results, IgG spice and herb results. Gut-wall body measurement may include measurements of calprotectin, eosinophil protein x (EPX), stool weight, pancreatic elastase, total urine volume, blood creatinine levels, blood lactulose levels, blood mannitol levels.

With continued reference to FIG. 1, gut-wall body measurement may include one or more elements of data describing one or more procedures examining gut including for example colonoscopy, endoscopy, large and small molecule challenge and subsequent urinary recovery using large molecules such as lactulose, polyethylene glycol-3350, and small molecules such as mannitol, L-rhamnose, polyethyleneglycol-400. Gut-wall body measurement may include data describing one or more images such as x-ray, MRI, CT scan, ultrasound, standard barium follow-through examination, barium enema, barium with contract, MRI fluoroscopy, positron emission tomography 9PET), diffusion-weighted MRI imaging, and the like.

With continued reference to FIG. 1, microbiome, as used herein, includes ecological community of commensal, symbiotic, and pathogenic microorganisms that reside on or within any of a number of human tissues and biofluids. For example, human tissues and biofluids may include the skin, mammary glands, placenta, seminal fluid, uterus, vagina, ovarian follicles, lung, saliva, oral mucosa, conjunctiva, biliary, and gastrointestinal tracts. Microbiome may include for example, bacteria, archaea, protists, fungi, and viruses. Microbiome may include commensal organisms that exist within a human being without causing harm or disease. Microbiome may include organisms that are not harmful but rather harm the human when they produce toxic metabolites such as trimethylamine. Microbiome may include pathogenic organisms that cause host damage through virulence factors such as producing toxic by-products. Microbiome may include populations of microbes such as bacteria and yeasts that may inhabit the skin and mucosal surfaces in various parts of the body. Bacteria may include for example *Firmicutes* species, *Bacteroidetes* species, *Proteobacteria* species, *Verrumicrobia* species, *Actinobacteria* species, *Fusobacteria* species, *Cyanobacteria* species and the like. Archaea may include methanogens such as *Methanobrevibacter* smithies' and *Methanosphaera stadtmanae*. Fungi may include *Candida* species and *Malassezia* species. Viruses may include bacteriophages. Microbiome species may vary in different locations throughout the body. For example, the genitourinary system may contain a high prevalence of *Lactobacillus* species while the gastrointestinal tract may contain a high prevalence of *Bifidobacterium* species while the lung may contain a high prevalence of *Streptococcus* and *Staphylococcus* species.

With continued reference to FIG. 1, microbiome body measurement may include one or more stool test results describing presence, absence, and/or measurement of microorganisms including bacteria, archaea, fungi, protozoa, algae, viruses, parasites, worms, and the like. Stool test results may contain species such as *Ackerman's muciniphila, Anaerotruncus colihominis*, bacteriology, Bacteroides vulgates', Bacteroides-*Prevotella*, *Barnesiella* species, *Bifidobacterium longarm*, *Bifidobacterium* species, *Butyrivbrio crossotus*, *Clostridium* species, *Collinsella aerofaciens*, fecal color, fecal consistency, *Coprococcus eutactus*, *Desulfovibrio piger*, *Escherichia coli*, *Faecalibacterium prausnitzii*, Fecal occult blood, *Firmicutes* to *Bacteroidetes* ratio, *Fusobacterium* species, *Lactobacillus* species, *Methanobrevibacter smithii*, yeast minimum inhibitory concentration, bacteria minimum inhibitory concentration, yeast mycology, fungi mycology, *Odoribacter* species, *Oxalobacter formigenes*, parasitology, *Prevotella* species, *Pseudoflavonifractor* species, *Roseburia* species, *Ruminococcus* species, *Veillonella* species and the like.

With continued reference to FIG. 1, microbiome body measurement may include one or more stool tests results that identify all microorganisms living a user's gut including bacteria, viruses, archaea, yeast, fungi, parasites, and bacteriophages. Microbiome body measurement may include DNA and RNA sequences from live microorganisms that may impact a user's health. Microbiome body measurement may include high resolution of both species and strains of all microorganisms. Microbiome body measurement may include data describing current microbe activity. Microbiome body measurement may include expression of levels of active microbial gene functions. Microbiome body measurement may include descriptions of sources of disease causing microorganisms, such as viruses found in the gastrointestinal tract such as raspberry bushy swarf virus from consuming contaminated raspberries or Pepino mosaic virus from consuming contaminated tomatoes.

With continued reference to FIG. 1, microbiome body measurement may include one or more blood test results that identify metabolites produced by microorganisms. Metabolites may include for example, indole-3-propionic acid, indole-3-lactic acid, indole-3-acetic acid, tryptophan, serotonin, kynurenine, total indoxyl sulfate, tyrosine, xanthine, 3-methylxanthine, uric acid, and the like.

With continued reference to FIG. 1, microbiome body measurement may include one or more breath test results that identify certain strains of microorganisms that may be present in certain areas of a user's body. This may include for example, lactose intolerance breath tests, methane-based breath tests, hydrogen based breath tests, fructose based breath tests. *Helicobacter pylori* breath test, fructose intolerance breath test, bacterial overgrowth syndrome breath tests and the like.

With continued reference to FIG. 1, microbiome body measurement may include one or more urinary analysis results for certain microbial strains present in urine. This may include for example, urinalysis that examines urine specific gravity, urine cytology, urine sodium, urine culture, urinary calcium, urinary hematuria, urinary glucose levels, urinary acidity, urinary protein, urinary nitrites, bilirubin, red blood cell urinalysis, and the like.

With continued reference to FIG. 1, nutrient as used herein, includes any substance required by the human body to function. Nutrients may include carbohydrates, protein, lipids, vitamins, minerals, antioxidants, fatty acids, amino acids, and the like. Nutrients may include for example vitamins such as thiamine, riboflavin, niacin, pantothenic acid, pyridoxine, biotin, folate, cobalamin, Vitamin C, Vitamin A, Vitamin D, Vitamin E, and Vitamin K. Nutrients may include for example minerals such as sodium, chloride, potassium, calcium, phosphorous, magnesium, sulfur, iron, zinc, iodine, selenium, copper, manganese, fluoride, chromium, molybdenum, nickel, aluminum, silicon, vanadium, arsenic, and boron.

With continued reference to FIG. 1, nutrients may include extracellular nutrients that are free floating in blood and exist outside of cells. Extracellular nutrients may be located in serum. Nutrients may include intracellular nutrients which may be absorbed by cells including white blood cells and red blood cells.

With continued reference to FIG. 1, nutrient body measurement may include one or more blood test results that identify extracellular and intracellular levels of nutrients. Nutrient body measurement may include blood test results that identify serum, white blood cell, and red blood cell levels of nutrients. For example, nutrient body measurement may include serum, white blood cell, and red blood cell levels of micronutrients such as Vitamin A, Vitamin B1, Vitamin B2, Vitamin B3, Vitamin B6, Vitamin B12, Vitamin B5, Vitamin C, Vitamin D, Vitamin E, Vitamin K1, Vitamin K2, and folate.

With continued reference to FIG. 1, nutrient body measurement may include one or more blood test results that identify serum, white blood cell and red blood cell levels of nutrients such as calcium, manganese, zinc, copper, chromium, iron, magnesium, copper to zinc ratio, choline, inositol, carnitine, methylmalonic acid (MMA), sodium, potassium, asparagine, glutamine, serine, coenzyme q10, cysteine, alpha lipoic acid, glutathione, selenium, eicosatetraenoic acid (EPA), docosahexaenoic acid (DHA), docosapentaenoic acid (DPA), total omega-3, lauric acid, arachidonic acid, oleic acid, total omega 6, and omega 3 index.

With continued reference to FIG. 1, nutrient body measurement may include one or more salivary test results that identify levels of nutrients including any of the nutrients as described herein. Nutrient body measurement may include hair analysis of levels of nutrients including any of the nutrients as described herein.

With continued reference to FIG. 1, genetic as used herein, includes any inherited trait. Inherited traits may include genetic material contained with DNA including for example, nucleotides. Nucleotides include adenine (A), cytosine (C), guanine (G), and thymine (T). Genetic information may be contained within the specific sequence of an individual's nucleotides and sequence throughout a gene or DNA chain. Genetics may include how a particular genetic sequence may contribute to a tendency to develop a certain disease such as cancer or Alzheimer's disease.

With continued reference to FIG. 1, genetic body measurement may include one or more results from one or more blood tests, hair tests, skin tests, urine, amniotic fluid, buccal swabs and/or tissue test to identify a user's particular sequence of nucleotides, genes, chromosomes, and/or proteins. Genetic body measurement may include tests that example genetic changes that may lead to genetic disorders. Genetic body measurement may detect genetic changes such as deletion of genetic material or pieces of chromosomes that may cause Duchenne Muscular Dystrophy. Genetic body measurement may detect genetic changes such as insertion of genetic material into DNA or a gene such as the BRCA1 gene that is associated with an increased risk of breast and ovarian cancer due to insertion of 2 extra nucleotides. Genetic body measurement may include a genetic change such as a genetic substitution from a piece of genetic material that replaces another as seen with sickle cell anemia where one nucleotide is substituted for another. Genetic body measurement may detect a genetic change such as a duplication when extra genetic material is duplicated one or more times within a person's genome such as with Charcot-Marie Tooth disease type 1. Genetic body measurement may include a genetic change such as an amplification when there is more than a normal number of copies of a gene in a cell such as HER2 amplification in cancer cells. Genetic body measurement may include a genetic change such as a chromosomal translocation when pieces of chromosomes break off and reattach to another chromosome such as with the BCR-ABL1 gene sequence that is formed when pieces of chromosome 9 and chromosome 22 break off and switch places. Genetic body measurement may include a genetic change such as an inversion when one chromosome experiences two breaks and the middle piece is flipped or inverted before reattaching. Genetic body measurement may include a repeat such as when regions of DNA contain a sequence of nucleotides that repeat a number of times such as for example in Huntington's disease or Fragile X syndrome. Genetic body measurement may include a genetic change such as a trisomy when there are three chromosomes instead of the usual pair as seen with Down syndrome with a trisomy of chromosome 21, Edwards syndrome with a trisomy at chromosome 18 or Patau syndrome with a trisomy at chromosome 13. Genetic body measurement may include a genetic change such as monosomy such as when there is an absence of a chromosome instead of a pair, such as in Turner syndrome.

With continued reference to FIG. 1, genetic body measurement may include an analysis of COMT gene that is responsible for producing enzymes that metabolize neurotransmitters. Genetic body measurement may include an analysis of DRD2 gene that produces dopamine receptors in the brain. Genetic body measurement may include an analysis of ADRA2B gene that produces receptors for noradrenaline. Genetic body measurement may include an analysis of 5-HTTLPR gene that produces receptors for serotonin. Genetic body measurement may include an analysis of BDNF gene that produces brain derived neurotrophic factor. Genetic body measurement may include an analysis of 9p21 gene that is associated with cardiovascular disease risk. Genetic body measurement may include an analysis of APOE gene that is involved in the transportation of blood lipids such as cholesterol. Genetic body measurement may include an analysis of NOS3 gene that is involved in producing enzymes involved in regulating vaso-dilation and vaso-constriction of blood vessels.

With continued reference to FIG. 1, genetic body measurement may include ACE gene that is involved in producing enzymes that regulate blood pressure. Genetic body measurement may include SLCO1B1 gene that directs pharmaceutical compounds such as statins into cells. Genetic body measurement may include FUT2 gene that produces enzymes that aid in absorption of Vitamin B12 from digestive tract. Genetic body measurement may include MTHFR gene that is responsible for producing enzymes that aid in metabolism and utilization of Vitamin B9 or folate. Genetic body measurement may include SHMT1 gene that aids in production and utilization of Vitamin B9 or folate. Genetic body measurement may include MTRR gene that produces enzymes that aid in metabolism and utilization of Vitamin B12. Genetic body measurement may include MTR gene that produces enzymes that aid in metabolism and utilization of Vitamin B12. Genetic body measurement may include FTO gene that aids in feelings of satiety or fulness after eating. Genetic body measurement may include MC4R gene that aids in producing hunger cues and hunger triggers. Genetic body measurement may include APOA2 gene that directs body to produce ApoA2 thereby affecting absorption of saturated fats. Genetic body measurement may include UCP1 gene that aids in controlling metabolic rate and thermoregulation of body. Genetic body measurement may include TCF7L2 gene that regulates insulin secretion. Genetic body measurement may include AMY1 gene that aids in digestion of starchy foods. Genetic body measurement may include MCM6 gene that controls production of lactase enzyme that aids in digesting lactose found in dairy products. Genetic body measurement may include BCMO1 gene that aids in producing enzymes that aid in metabolism and activation of Vitamin A. Genetic body measurement may include SLC23A1 gene that produce and transport Vitamin C. Genetic body measurement may include CYP2R1 gene that produce enzymes involved in production and activation of Vitamin D. Genetic body measurement may include GC gene that produce and transport Vitamin D. Genetic body measurement may include CYP1A2 gene that aid in metabolism and elimination of caffeine. Genetic body measurement may include CYP17A1 gene that produce enzymes that convert progesterone into androgens such as androstenedione, androstendiol, dehydroepiandrosterone, and testosterone.

With continued reference to FIG. 1, genetic body measurement may include CYP19A1 gene that produce enzymes that convert androgens such as androstenedione and testosterone into estrogens including estradiol and estrone. Genetic body measurement may include SRD5A2 gene that aids in production of enzymes that convert testosterone into dihydrotestosterone. Genetic body measurement may include UFT2B17 gene that produces enzymes that metabolize testosterone and dihydrotestosterone. Genetic body measurement may include CYP1A1 gene that produces enzymes that metabolize estrogens into 2 hydroxy-estrogen. Genetic body measurement may include CYP1B1 gene that produces enzymes that metabolize estrogens into 4 hydroxy-estrogen. Genetic body measurement may include CYP3A4 gene that produces enzymes that metabolize estrogen into 16 hydroxy-estrogen. Genetic body measurement may include COMT gene that produces enzymes that metabolize 2 hydroxy-estrogen and 4 hydroxy-estrogen into methoxy estrogen. Genetic body measurement may include GSTT1 gene that produces enzymes that eliminate toxic by-products generated from metabolism of estrogens. Genetic body measurement may include GSTM1 gene that produces enzymes responsible for eliminating harmful by-products generated from metabolism of estrogens. Genetic body measurement may include GSTP1 gene that produces enzymes that eliminate harmful by-products generated from metabolism of estrogens. Genetic body measurement may include SOD2 gene that produces enzymes that eliminate oxidant by-products generated from metabolism of estrogens.

With continued reference to FIG. 1, metabolic, as used herein, includes any process that converts food and nutrition into energy. Metabolic may include biochemical processes that occur within the body. Metabolic body measurement may include blood tests, hair tests, skin tests, amniotic fluid, buccal swabs and/or tissue test to identify a user's metabolism. Metabolic body measurement may include blood tests that examine glucose levels, electrolytes, fluid balance, kidney function, and liver function. Metabolic body measurement may include blood tests that examine calcium levels, albumin, total protein, chloride levels, sodium levels, potassium levels, carbon dioxide levels, bicarbonate levels, blood urea nitrogen, creatinine, alkaline phosphatase, alanine amino transferase, aspartate amino transferase, bilirubin, and the like.

With continued reference to FIG. 1, metabolic body measurement may include one or more blood, saliva, hair, urine, skin, and/or buccal swabs that examine levels of hormones within the body such as 11-hydroxy-androsterone, 11-hydroxy-etiocholanolone, 11-keto-androsterone, 11-keto-etiocholanolone, 16 alpha-hydroxyestrone, 2-hydroxyestrone, 4-hydroxyestrone, 4-methoxyestrone, androstanediol, androsterone, creatinine, DHEA, estradiol, estriol, estrone, etiocholanolone, pregnanediol, pregnanestriol, specific gravity, testosterone, tetrahydrocortisol, tetrahydrocrotisone, tetrahydrodeoxycortisol, allo-tetrahydrocortisol.

With continued reference to FIG. 1, metabolic body measurement may include one or more metabolic rate test results such as breath tests that may analyze a user's resting metabolic rate or number of calories that a user's body burns each day rest. Metabolic body measurement may include one or more vital signs including blood pressure, breathing rate, pulse rate, temperature, and the like. Metabolic body measurement may include blood tests such as a lipid panel such as low density lipoprotein (LDL), high density lipoprotein (HDL), triglycerides, total cholesterol, ratios of lipid levels such as total cholesterol to HDL ratio, insulin sensitivity test, fasting glucose test, Hemoglobin A1C test, adipokines such as leptin and adiponectin, neuropeptides such as ghrelin, pro-inflammatory cytokines such as interleukin 6 or tumor necrosis factor alpha, anti-inflammatory cytokines such as interleukin 10, markers of antioxidant status such as oxidized low-density lipoprotein, uric acid, paraoxonase 1. Persons skilled in the art, upon reviewing the entirety of this disclosure, will be aware of various additional examples of biological state data that may be used consistently with descriptions of systems and methods as provided in this disclosure.

With continued reference to FIG. 1, biological data may be obtained from a physically extracted sample. A "physical sample" as used in this example, may include any sample obtained from a human body of a user. A physical sample may be obtained from a bodily fluid and/or tissue analysis such as a blood sample, tissue, sample, buccal swab, mucous sample, stool sample, hair sample, fingernail sample and the like. A physical sample may be obtained from a device in contact with a human body of a user such as a microchip embedded in a user's skin, a sensor in contact with a user's skin, a sensor located on a user's tooth, and the like. Biological data may be obtained from a physically extracted sample. A physical sample may include a signal from a sensor configured to detect biological data of a user and record biological data as a function of the signal. A sensor may include any medical sensor and/or medical device configured to capture sensor data concerning a patient, including any scanning, radiological and/or imaging device such as without limitation x-ray equipment, computer assisted tomography (CAT) scan equipment, positron emission tomography (PET) scan equipment, any form of magnetic resonance imagery (MRI) equipment, ultrasound equipment, optical scanning equipment such as photo-plethysmography equipment, or the like. A sensor may include any electromagnetic sensor, including without limitation electroencephalographic sensors, magnetoencephalographic sensors, electrocardiographic sensors, electromyographic sensors, or the like. A sensor may include a temperature sensor. A sensor may include any sensor that may be included in a mobile device and/or wearable device, including without limitation a motion sensor such as an inertial measurement unit (IMU), one or more accelerometers, one or more gyroscopes, one or more magnetometers, or the like. At least a wearable and/or mobile device sensor may capture step, gait, and/or other mobility data, as well as data describing activity levels and/or physical fitness. At least a wearable and/or mobile device sensor may detect heart rate or the like.

A sensor may detect any hematological parameter including blood oxygen level, pulse rate, heart rate, pulse rhythm, blood sugar, and/or blood pressure. A sensor may be configured to detect internal and/or external biomarkers and/or readings. A sensor may be a part of system 100 or may be a separate device in communication with system 100.

With continued reference to FIG. 1, a biological profile includes a prescriptive therapy indicator. A "prescriptive therapy" as used in this disclosure, is any medicine, drug, supplement, food, ingredient or other substance which has a physiological effect when ingested or otherwise introduced into the body. A drug may include any chemical substance that may produce a biological effect when administered to a living organism. A drug may include any medication or medicine that is utilized to treat, cure, prevent, or diagnose a disease or to promote well-being. A drug may be produced by organic synthesis. A drug may be extracted from medicinal plants. A drug may be administered by one or more routes of administration including intravenous administration, intramuscular administration, intrathecal administration, subcutaneous administration, inhaled administration, dry powder administration, injectable administration, solution administration, suspension administration, emulsion administration, intraperitoneal administration, intraosseous administration, insufflation administration, oral administration, rectal administration, sublingual administration, topical administration, vaginal administration and the like. A drug may be available only with a prescription, which may include any instrument written by a medical practitioner that authorizes a user to be provided a medicine or treatment. A medical practitioner may include any medical professional who may be licensed by any state and/or federal licensing agency that may grant the medical professional authority to prescribe a medicine, drug, and/or treatment. A prescriptive therapy may include food, such as for example a list of one or more foods that a user should or should not consume. A prescriptive therapy may include a supplement, including any product that contains one or more ingredients intended to supplement one's diet. A supplement may include for example any vitamin, mineral, nutrient, homeopathic, amino acid, herb, botanical, nutraceutical, enzyme, health food, medical food, and the like. For example, a supplement may include a multi-vitamin or a cod liver oil supplement. A supplement may be available with and/or without a prescription from a health care professional.

With continued reference to FIG. 1, a "prescriptive therapy indicator" as used in this disclosure, is one or more factors that may affect the administration and/or metabolism of one or more prescriptive therapies. Factors of prescriptive therapy metabolism may include one or more genetic factors. Genetic factors may include a person's genetic ability to absorb, distribute, metabolize, and excrete a prescriptive therapy. Genetic factors may include a user's body weight, genetic conditions, genetic polymorphisms of drug metabolizing enzymes, height, race, drug receptor sensitivity, and sex. Influencers of prescriptive therapy metabolism may include one or more biological factors. Biological factors may include a person's biological ability to absorb, distribute, metabolize, and excrete a prescriptive therapy. Biological factors may include age, alcohol use, body weight, cardiovascular function, diet, diseases, co-morbid conditions, height, kidney function, liver function, drug receptor sensitivity, smoking status, and stress. Influencers of prescriptive therapy metabolism may include one or more ecological factors. Ecological factors may include alcohol use, climate where a user resides, culture, educational status, language, socioeconomic factors, diet, prescriptive therapy adherence, prescriptive therapy compliance, medical practices, medical beliefs, pollution, smoking status, stress, sunlight exposure, and therapeutic approach.

With continued reference to FIG. 1, system 100 may include user profile database 124. User profile database 124 may store one or more user biological profile 112. User profile database 124 may be implemented, without limitation, as a relational database, a key-value retrieval datastore such as a NOSQL database, or any other form or structure for use as a datastore that a person skilled in the art would recognize as suitable upon review of the entirety of this disclosure.

With continued reference to FIG. 1, computing device 104 is configured to generate an unsupervised machine-learning model 128 using the compositional training data 108. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like. Unsupervised machine-learning model 128 may include, without limitation, one or more machine-learning algorithms including clustering algorithms and/or cluster analysis processes, such as without limitation hierarchical clustering, centroid clustering, distribution clustering, clustering using density models, subspace models, group models, graph-based models, signed graph models, neural models, k-means clustering, OPTICS algorithm, local outlier factor, autoencoders, deep belief nets, Hebbian learning, generative adversarial networks, self-organizing map, expectation-maximization algorithm, methods of moments, blind signal separation techniques, or the like. Unsupervised learning may be performed by neural networks and/or deep learning protocols as described below.

Continuing to refer to FIG. 1, machine-learning processes as described in this disclosure may be used to generate machine-learning models. A machine-learning model, as used herein, is a mathematical representation of a relationship between inputs and outputs, as generated using any machine-learning process as described above, and stored in memory; an input is submitted to a machine-learning model once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model may be generated by creating an artificial neural network, such as a convolutional neural network comprising an input layer of nodes, one or more intermediate layers, and an output layer of nodes. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

With continued reference to FIG. 1, generating an unsupervised machine-learning algorithm may include generating a clustering algorithm. Clustering algorithm may include a process of grouping a set of data in such a way that data in the same group or cluster are more similar to each other than to those in other clusters. Clustering algorithm may include generating one or more clustering algorithms including hierarchical clustering, k-means clustering, mixture models, density-based spatial clustering of applications with noise (DBSCAN), ordering points to identify clustering structure (OPTICS), biclustering, highly connected subgraph (HCS) clustering, and the like. Clustering algorithm may include generating one or more clustering models. Clustering models may include connectivity models, centroid models, distribution models, density models, subspace models, group models, graph-based models, signed graph models, neural models and the like. Clustering algorithms may include hard clustering where data may belong to a cluster or not. Clustering algorithms may include soft clustering where data may belong to each cluster to a certain degree. Clustering algorithms may include strict partitioning clusters where data belongs to exactly one cluster. Clustering algorithms may include strict partitioning clusters with outliers where data may not belong to any cluster and may be considered an outlier. Clustering algorithms may include overlapping clustering where data may belong to more than one cluster such as in hard clusters. Clustering algorithms may include hierarchical clusters where data may belong to a child cluster while also belonging to a parent cluster. Clustering algorithms may include subspace clustering.

With continued reference to FIG. 1, generating an unsupervised machine-learning algorithm may include generating a k-means clustering algorithm. A "k-means clustering algorithm" as used in this disclosure, includes cluster analysis that partitions n observations or unclassified cluster data entries into k clusters in which each observation or unclassified cluster data entry belongs to the cluster with the nearest mean. Cluster data entry may include data entries selected from a clustering dataset. Cluster data entry may be received from clustering database. "Cluster analysis" as used in this disclosure, includes grouping a set of observations or data entries in way that observations or data entries in the same group or cluster are more similar to each other than to those in other groups or clusters. Cluster analysis may be performed by various cluster models that include connectivity models such as hierarchical clustering, centroid models such as k-means, distribution models such as multivariate normal distribution, density models such as density-based spatial clustering of applications with nose (DBSCAN) and ordering points to identify the clustering structure (OPTICS), subspace models such as biclustering, group models, graph-based models such as a clique, signed graph models, neural models, and the like. Cluster analysis may include hard clustering whereby each observation or unclassified cluster data entry belongs to a cluster or not. Cluster analysis may include soft clustering or fuzzy clustering whereby each observation or unclassified cluster data entry belongs to each cluster to a certain degree such as for example a likelihood of belonging to a cluster. Cluster analysis may include strict partitioning clustering whereby each observation or unclassified cluster data entry belongs to exactly one cluster. Cluster analysis may include strict partitioning clustering with outliers whereby observations or unclassified cluster data entries may belong to no cluster and may be considered outliers. Cluster analysis may include overlapping clustering whereby observations or unclassified cluster data entries may belong to more than one cluster. Cluster analysis may include hierarchical clustering whereby observations or unclassified cluster data entries that belong to a child cluster also belong to a parent cluster.

With continued reference to FIG. 1, k-means clustering module generates a k-means clustering algorithm containing unclassified data as input and outputs a definite number of classified data entry cluster wherein the data entry clusters each contain cluster data entries. K-means clustering module may select a specific number of groups or clusters to output, identified by the variable "k." Generating a k-means clustering algorithm includes assigning inputs containing unclassified data to a "k-group" or "k-cluster" based on feature similarity. Centroids of k-groups or k-clusters may be utilized to generate classified data entry cluster. K-means clustering module by select "k" variable by calculating k-means clustering algorithm for a range of k values and comparing results. K-means clustering module may compared results across different values of k as the mean distance between cluster data entries and cluster centroid. K-means clustering module may calculate mean distance to a centroid as a function of k value, and the location of where the rate of decrease starts to sharply shift, this may be utilized to select a k value. Centroids of k-groups or k-cluster include a collection of feature values which are utilized to classify data entry clusters containing cluster data entries. K-means clustering module may select a k value by classifying a biological profile. K-means clustering module may evaluate a biological profile to evaluate one or more unsupervised feature 132 that may be used by computing device 104 to generate an unsupervised machine-learning algorithm including a k-means clustering algorithm. An "unsupervised feature" as used in this disclosure, is a trait or characteristic that is utilized to select and/or generate an unsupervised machine learning algorithm. An unsupervised feature 132 may include any individual measurable property or characteristic of a phenomenon being observed. An unsupervised feature 132 may match one or more prescriptive therapy treatment indicators. Computing device 104 may select one or more prescriptive therapy treatment indicators to generate one or more unsupervised machine-learning algorithms. An unsupervised feature 132 may be utilized to select a particular unsupervised model such as a k-means clustering model or a hierarchical clustering model. An unsupervised feature 132 may be utilized to determine how many clustering groups to generate, if a clustering model should be generated as a hard clustering algorithm or a soft clustering algorithm. An unsupervised feature 132 may be selected from one or more prescriptive therapy indicators contained within a biological profile. An unsupervised feature 132 may be utilized to select one or more therapy response model 136 that matches or contains data entries related to an unsupervised feature 132 and one or more prescriptive therapy indicators. Computing device 104 may select one or more unsupervised feature 132 to generate one or more unsupervised machine-learning algorithms. Computing device 104 utilizes an unsupervised feature 132 to select a definite number of classified data entry cluster or k-value. In an embodiment, a particular unsupervised feature 132 may indicate a preferred k-value based on previous data collections and calculations. For instance and without limitation, an unsupervised feature 132 that indicates decreased liver function may be best suited for a k-value of 71 while an unsupervised feature 132 that indicates a user with an eastern European background may be best suited for a k-value of 11. In yet another non-limiting example, an unsupervised feature 132 such as a genetic polymorphism to one or more cytochrome p450 enzymes involved in the metabolism of one or more prescriptive therapies may be best suited to a clustering algorithm whereas an unsupervised feature 132 such as a user's race and cultural background may be best suited for a neural network model.

With continued reference to FIG. 1, an unsupervised feature 132 may be selected by computing device 104 based on one or more prescriptive therapy indicators contained within a biological profile. Unsupervised feature 132 may be categorized according to one or more influencers of prescriptive therapy metabolism. Unsupervised feature 132 may include one or more genetic features. Genetic features, as used in this disclosure, are one or more genetic influences that affect administration of a prescriptive therapy. Genetic features may include the ability of a user to absorb, distribute, metabolize, and excrete one or more prescriptive therapies. Genetic features may include body weight, genetic conditions, genetic polymorphism of drug metabolizing enzymes, height, race, prescriptive therapy receptor sensitivity, and sex. Unsupervised feature 132 may include one or more biological features. Biological features may include absorption, distribution, metabolism, and excretion of a user to metabolize one or more prescriptive therapies. Biological features may include age, alcohol use, body weight, cardiovascular function, diet, concurrent diseases or diagnoses, height, kidney function, liver function, prescriptive therapy receptor sensitivity, smoking status, and stress. Unsupervised feature 132 may include one or more extrinsic factors. Extrinsic factors may include alcohol use, climate, culture, educational status, language, socioeconomic factors, current diagnoses, diet, co-morbid diseases and conditions, prescriptive therapy adherence, medical practices, prescriptive therapy compliance, medical practices, pollution, smoking status, stress, sunlight exposure, and therapeutic approach. Computing device 104 may select an unsupervised feature 132 as a function of a user biological profile 112. For instance and without limitation, a user biological profile 112 that contains a prescriptive therapy indicator that indicates the user has reduced receptor sensitivity to a particular prescriptive therapy indicator may be utilized to select an unsupervised feature 132 to reflect this. Computing device 104 may then utilize the particular unsupervised feature 132 to select a particular unsupervised machine-learning algorithm or to select a particular number of data clusters for a clustering algorithm or to select compositional training data 108 that contain data entries that reflect this reduced receptor sensitivity. Additionally or alternatively, computing device 104 may utilize an unsupervised feature 132 to select a particular therapy response model 136 selected as an output of generating an unsupervised machine-learning algorithm.

With continued reference to FIG. 1, computing device 104 is configured to select a therapy response model 136 as a function of generating an unsupervised machine-learning model 128. A "therapy response model 136" as used in this disclosure, includes a machine-learning model that utilizes a biological profile as an input and outputs a prescriptive therapy label 140. Machine-learning model includes any of the machine-learning models as described herein. A machine-learning model may include performing a series of one or more calculations, algorithms, and/or equations. A machine-learning model may be generated using one or more machine-learning algorithms. Therapy response model 136 may consider one or more prescriptive therapy indicators that may affect the metabolism of one or more prescriptive therapies. For instance and without limitation, computing device 104 may contain a plurality of therapy response model 136. A first therapy response model 136 may be best suited for a user who is of Asian ancestry, doesn't smoke, and exhibits a cytochrome p450 phenotype CYP2C19*2 indicating reduced clearance of prescriptive therapies such as antidepressants including citalopram and benzodiazepines such as diazepam. A second therapy response model 136 may be best suited for a user who is female, abuses alcohol, and lives in a sub-tropical climate. In an embodiment, a therapy response model may be selected based on a current and/or preexisting condition that the user may have been diagnosed with. A "prescriptive therapy label" as used in this disclosure, is an indicator as to whether or not a prescriptive therapy should be consumed by a user. A prescriptive therapy label may include a negative indicator such as "not compatible" when a prescriptive therapy is not compatible with a user's body. A prescriptive therapy label 140 may include a positive indicator such as "compatible" when a prescriptive therapy is compatible with a user's body. For instance and without limitation, a prescriptive therapy label 140 may indicate that a prescriptive therapy such as SYNTHROID as produced by Abbott Laboratories of Chicago, Illinois may be compatible with a user while a prescriptive therapy such as CYTOMEL as produced by Pfizer of New York, New York may not be compatible with a user. A prescriptive therapy label 140 may include an indicator as to whether or not a prescriptive therapy should be consumed by a user or not in regard to one or more prescriptive therapy classes. For instance and without limitation, a prescriptive therapy label 140 may indicate that a user can consume statins, but a user is unable to tolerate fibric acid derivatives. In yet another non-limiting example, a prescriptive therapy label 140 may indicate that a user can consume cephalosporins, but a user is unable to consume tetracyclines.

With continued reference to FIG. 1, computing device 104 is configured to select a therapy response model 136 as a function of generating an unsupervised machine-learning algorithm. Unsupervised machine-learning algorithm includes any of the unsupervised machine-learning algorithms as described above.

With continued reference to FIG. 1, computing device 104 is configured to receive from a remote device 144 a proposed prescriptive therapy. Remote device 144 may include without limitation, a display in communication with computing device 104, where a display may include any display as described herein. Remote device 144 may include an additional computing device, such as a mobile device, laptop, desktop, computer and the like. Remote device 144 may transmit and/or receive one or more inputs from computing device 104 utilizing any network methodology as described herein. Remote device 144 may be operated by a user which may include any human subject. Remote device 144 may be operated by an informed advisor. An informed advisor may include any medical professional who may assist and/or participate in the medical treatment of a user. An informed advisor may include a medical doctor, nurse, physician assistant, pharmacist, yoga instructor, nutritionist, spiritual healer, meditation teacher, fitness coach, health coach, life coach, and the like Remote device 144 may be operated by a family member or friend of a user. For instance and without limitation, remote device 144 may be operated by an informed advisor such as user's functional medicine doctor who may generate a proposed prescriptive therapy to determine if a new prescriptive therapy for multiple sclerosis is compatible with a user. Proposed prescriptive therapy may be transmitted from a remote device 144 to computing device 104 utilizing any network methodology as described herein.

With continued reference to FIG. 1, a "proposed prescriptive therapy 148" as used in this disclosure, includes one or more prescriptive therapies that are being considered as possible treatment options for a user. A proposed prescriptive therapy may be considered for one or more concurrent or pre-existing medical conditions. A proposed prescriptive therapy 148 may identify a brand name prescriptive therapy such as GLUCOPHAGE as produced by Bristol Myers Squib of New York, New York A proposed prescriptive therapy 148 may identify a generic name prescriptive therapy such as simvastatin or sildenafil. A proposed prescriptive therapy 148 may identify a class of prescriptive therapies such as antibiotics, analgesics, antipyretics, quinolones, beta-blockers, and the like. A proposed prescriptive therapy 148 may identify a particular function of a prescriptive therapy such as birth control, anti-hypertensives, muscle relaxant and the like. A proposed prescriptive therapy 148 may identify a particular chemical class of prescriptive therapies such as benzodiazepines or cardiac glycosides. A proposed prescriptive therapy 148 may identify a mechanism of action such as ACE inhibitors, incretin mimetic, proton-pump inhibitor and the like. A proposed prescriptive therapy 148 may identify a mode of action such as diuretics, bronchodilators, antifungals and the like. A proposed prescriptive therapy 148 may identify a therapeutic class such as anticoagulants, antidepressants, sedatives and the like. A proposed prescriptive therapy 148 may identify a diagnosis and seek to identify one or more prescriptive therapies that may be utilized to treat the diagnosis. For example, a proposed prescriptive therapy 148 may identify a diagnosis such as "Type Two Diabetes Mellites" or "Rheumatoid Arthritis."

With continued reference to FIG. 1, a proposed prescriptive therapy 148 may be generated by an informed advisor and transmitted to computing device 104 utilizing remote device 144. Informed advisor may include any of the informed advisors as described herein. Proposed prescriptive therapy 148 may be generated by a user and transmitted to computing device 104 utilizing remote device 144. For instance and without limitation, a user may receive a recent diagnosis of hypothyroidism and user may be curious as to what prescriptive therapies will be tolerated by user's body and what prescriptive therapies user may wish to discuss with user's functional medicine doctor at an upcoming visit.

With continued reference to FIG. 1, computing device 104 may include a graphical user interface 152. Graphical user interface 152 may include without limitation a form or other graphical element having data entry fields, wherein an informed advisor or user may select one or more fields to enter one or more proposed prescriptive therapies. Graphical user interface 152 may provide a drop-down menu and display prescriptive therapies where a user may select one or more proposed prescriptive therapies. Prescriptive therapies may be displayed according to one classification system for experts such as informed advisors and according to a second classification system for users who may not be skilled in medical language. For instance and without limitation, graphical user interface 152 may provide a drop-down menu of particular classes of prescriptive therapies that a user may select from where classes of prescriptive therapies may be organized according to what conditions they are used to treat such as by therapeutic indication. For example, graphical user interface 152 may display to a user one or more classes of prescriptive therapies that includes anti-hypertensives, antibiotics, therapies for high blood pressure, therapies for elevated testosterone and the like. Graphical user interface 152 may display to an informed advisor one or more classes of prescriptive therapies that may be organized according to mechanism of action, chemical class or chemical structure and the like. For instance and without limitation, graphical user interface 152 may display to an informed advisor chemical classes such as beta-lactam antibiotics, thiazide diuretics, cardiac glycosides and the like. In yet another non-limiting example, graphical user interface 152 may display to an informed advisor mechanism of action such as diuretics, inotropes, chronotropes, decongestants and the like. In an embodiment, graphical user interface 152 may provide one or more free form text fields where a user and/or informed advisor may type in one or more proposed prescriptive therapies. In an embodiment, graphical user interface 152 may display one or more photographs of one or more prescriptive therapies that a user and/or informed advisor may select on graphical user interface 152.

With continued reference to FIG. 1, computing device 104 is configured to create a therapy response model 136 utilizing a selected therapy response model 136 relating a biological profile to prescriptive therapy label 140. Therapy response model 136 may be created by generating one or more machine-learning algorithms. Machine-learning algorithms may be implemented using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure, Still referring to FIG. 1, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

With continued reference to FIG. 1, models may be generated using alternative or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using training data.

Still referring to FIG. 1, machine-learning algorithms may include supervised machine-learning algorithms. Supervised machine learning algorithms, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised machine-learning process may include a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data. Persons skilled in the art, upon reviewing the entirety of this disclosure, will be aware of various possible variations of supervised machine learning algorithms that may be used to determine relation between inputs and outputs.

With continued reference to FIG. 1, supervised machine-learning processes may include classification algorithm defined as processes whereby a computing device 104 derives, from training data, a model for sorting inputs into categories or bins of data. Classification may be performed using, without limitation, linear classifiers such as without limitation logistic regression and/or naïve Bayes classifiers, nearest neighbor classifiers including without limitation k-nearest neighbors classifiers, support vector machines, decision trees, boosted trees, random forest classifiers, and/or neural network-based classifiers.

With continued reference to FIG. 1, machine-learning algorithms may include unsupervised machine-learning algorithms. Unsupervised machine-learning algorithms may include any of the unsupervised machine-learning algorithms as described herein.

With continued reference to FIG. 1, computing device 104 is configured to identify a prescriptive therapy label 140 for a proposed prescriptive therapy 148. Prescriptive therapy label 140 may provide an indicator as to whether or not a proposed prescriptive therapy 148 is compatible or not compatible with a user's body. In an embodiment, computing device 104 may display one or more other suggested prescriptive therapies that may be compatible with a user's body if a proposed prescriptive therapy 148 is found not to be compatible with a user's body. For instance and without limitation, prescriptive therapy label 140 may indicate that a proposed prescriptive therapy 148 such as metformin is not compatible with a user's body but computing device 104 may suggest other prescriptive therapies such as glyburide or glipizide which both may be compatible with a user's body. In an embodiment, a prescriptive therapy label 140 may identify the compatibility or incompatibility of a particular class of prescriptive therapies such as the incompatibility of statins but the compatibility of fibrates. In an embodiment a prescriptive therapy label 140 may identify the compatibility or incompatibility of members of a class of prescriptive therapies such as the incompatibility of simvastatin and atorvastatin but the compatibility of fluvastatin, lovastatin, pravastatin, rosuvastatin, and pitavastatin.

With continued reference to FIG. 1, identifying a proposed prescriptive therapy 148 may include receiving contraindication training data 156. "Contraindication training data 156" as used in this disclosure includes training data that contains a plurality of data entries containing prescriptive therapies and correlated contraindications. A "contraindication" as used in this disclosure, is any reason as to why a prescriptive therapy should not be administered to a user because doing so may cause harm. Prescriptive therapies may cause harm when they are administered in combinations with other prescriptive therapies that could create potentially life threatening conditions due to the potential of drug interactions. Prescriptive therapies may cause harm when they may interact with other prescriptive therapies the user may be taking for other preexisting and/or concurrent medical conditions. Prescriptive therapies may cause harm when they may interact with other preexisting and/or concurrent medical conditions. For instance and without limitation, a contraindication may occur when a user who is undergoing chemotherapy for diagnosed cancer and is in an immune-compromised state and is given immune stimulating prescriptive therapies. Contraindications 160 may be evaluated on a continuum where absolute contraindications 160 may include a situation where there are no reasonable circumstances for consuming a prescriptive therapy. For example, a person with a preexisting medical condition such as hemochromatosis may have an absolute contraindication to iron preparations. Relative contraindications 160 may include a situation where a user may be at high risk of complications from a treatment, but the risks may be outweighed by other considerations or mitigated by other measurements. For example, a relative contraindication when a user with reduced renal function consumes two separate prescriptive therapies that are both heavily renally metabolized. In yet another non-limiting example, a relative contraindication may include a user with a diagnosed autoimmune condition currently being treated with one or more immune suppressing medications not consuming steroid medications at the same time or in conjunction with one or more immune suppressing medications. Computing device 104 may retrieve user current therapies. "User current therapies 164" as used in this disclosure, is any concurrent medications a user is currently taking and/or any current and/or preexisting medical conditions that a user may be diagnosed with. Medications may include both prescriptive, non-prescriptive, over the counter, and/or supplements. Medical conditions may include any disease, lesion, disorder, nonpathological condition, mental disorder, psychiatric condition, and the like. Computing device 104 generates a machine-learning model using the contraindication training data 156 wherein the machine-learning model utilizes prescriptive therapies as an input and outputs contraindications 160. Machine-learning model includes any of the machine-learning models as described above. Computing device 104 evaluates output contraindications 160. For example, computing device 104 may match output contraindications 160 to current prescriptive therapies to determine if any are the same. In such an instance, where an output contraindication is also listed as a current prescriptive therapy, computing device 104 may identify a prescriptive therapy label 140 for the proposed prescriptive therapy 148 as not being compatibility. In an embodiment, evaluating output contraindications 160 may include an instance where an output contraindication is not listed as a current prescriptive therapy. In such an instance, computing device 104 may identify a prescriptive therapy label 140 for the proposed prescriptive therapy 148 as compatible.

With continued reference to FIG. 1, identifying a prescriptive therapy label 140 includes receiving kinetic training data 168. "Kinetic training data 168" as used in this disclosure, is training data containing a plurality of data entries containing kinetic data and correlated prescriptive therapies. "Kinetic data" as used in this disclosure, includes an element of data describing how a body processes a prescriptive therapy. Kinetic data may include data relating to absorption, distribution, metabolism, and elimination of prescriptive therapies. Absorption may include the ability of a prescriptive therapy to reach a tissue such as via mucous surfaces such as intestinal absorption in the digestive tract. Absorption may be altered by factors such as poor solubility of a prescriptive therapy. For example, vancomycin contains very poor oral absorption and solubility, and as such is preferably administered intravenously. Absorption may also be altered by other factors such as gastric emptying time which can be affected by medical conditions such as diabetes that can cause gastroparesis and delayed gastrointestinal emptying time. Absorption may be altered by chemical instability of a prescriptive therapy in the stomach, and the inability of a prescriptive therapy to permeate the intestinal wall thereby reducing the extent to which a prescriptive therapy is absorbed. Absorption may also affect bioavailability of a prescriptive therapy as prescriptive therapy that are poorly absorbed may have very little bioavailability and as such may need to be administered in an alternative dosage form. Distribution may include the ability of a prescriptive therapy to be carried to its effector site, such as through the bloodstream. After passage through the bloodstream, a prescriptive therapy may be distributed to one or more muscles and organs. The ability of a prescriptive therapy to be distributed to one or more locations in the body may be affected by factors such as regional blood flow rates, molecular size, polarity and binding to serum proteins, and forming a complex. For example, a prescriptive therapy such as levocarnitine is unable to be distributed across the blood brain barrier and as such acts systemically in the body outside of the blood brain barrier, while acetyl-1-carnitine is able to be distributed across the blood brain barrier and is effectively utilized for neurological conditions including memory issues and tremors seen in individuals with Parkinson's disease. Metabolism includes the ability of a prescriptive therapy to be broken down as it enters the body. Metabolism may be carried out by the liver through redox enzymes or cytochrome P450 enzymes. As a prescriptive therapy is metabolized, it may be converted to one or more new compounds known as metabolites. Excretion includes the ability of a prescriptive therapy and its metabolites to be removed from the body via excretion such as through the kidneys and eventually into urine and/or in the feces. Excretion can occur at the kidneys where a prescriptive therapy is excreted into urine. Excretion can occur in biliary tract where excretion begins in the liver and passes through to the gut until the prescriptive therapy is excreted in urine or fecal elimination. Excretion can occur through the lungs such as by exhaling a prescriptive therapy or its metabolites.

With continued reference to FIG. 1, computing device 104 retrieves an element of user kinetic data. In an embodiment, user kinetic data may be stored in user profile database 124. Computing device 104 generates a machine-learning model using the kinetic training data 168 wherein the machine-learning model utilizes an element of user kinetic data as an input and outputs compatible prescriptive therapies 172. Machine-learning model may include any of the machine-learning models as described above. Computing device 104 compares output compatible prescriptive therapies 172 to proposed prescriptive therapy 148. Computing device 104 may identify proposed prescriptive therapy 148 as a compatible therapy if proposed prescriptive therapy 148 matches to an output compatible prescriptive therapy. Computing device 104 may identify proposed prescriptive therapy 148 as an incompatible therapy if proposed prescriptive therapy 148 does not match to an output compatible prescriptive therapy. In such an instance, computing device may propose an alternative suggestive prescriptive therapy based on output compatible prescriptive therapies 172.

With continued reference to FIG. 1, identifying a prescriptive therapy label 140 includes receiving genetic training data 176. "Genetic training data 176" as used herein, includes training data that includes a plurality of data entries containing genetic data and correlated prescriptive therapies. "Genetic data" as used herein, includes deoxyribonucleic acid (DNA) samples and/or sequences, such as without limitation DNA sequences contained in one or more chromosomes in human cells. Genetic data may include, without limitation, ribonucleic acid (RNA) samples and/or sequences, such as samples and/or sequences of messenger RNA (mRNA) or the like taken from human cells. Genetic data may include telomere lengths. Genetic data may include epigenetic data including data describing one or more states of methylation of genetic material. Genetic data may include one or more polymorphisms of P450 cytochromes. For instance and without limitation, genetic data may include one or more polymorphisms of CYP2C19 enzyme that may demonstrate a user is a hyper metabolizer of certain prescriptive therapies such as proton pump inhibits, citalopram, diazepam, and imipramine. In yet another non-limiting example, genetic data may include one or more markers of cardiovascular function such as a genetic polymorphism that leads to reduced activity of beta-one adrenergic receptors thereby resulting in reduced efficacy of prescriptive therapies that work on beta-one adrenergic receptors such as metoprolol.

With continued reference to FIG. 1, computing device 104 retrieves an element of user genetic data 180. Computing device 104 may retrieve an element of user genetic data 180 from user profile database 124 for example. Computing device 104 generates a machine-learning model using the genetic training data 176 wherein the machine-learning model utilizes the element of user genetic data 180 as an input and outputs compatible prescriptive therapies 172. Machine-learning model includes any of the machine-learning models as described herein. Machine-learning models may include any of the machine-learning models as described herein. Computing device 104 identifies a prescriptive therapy label 140 as a function of generating a machine-learning model. For instance and without limitation, an output compatible prescriptive therapy that matches a proposed prescriptive therapy 148 may be utilized to identify a prescriptive therapy label 140 as compatible. In yet another non-limiting example, an output compatible prescriptive therapy that does not match a proposed prescriptive therapy 148 may be utilized to identify a prescriptive therapy label 140 as incompatible.

With continued reference to FIG. 1, computing device 104 is configured to receive a prescriptive therapy label. A prescriptive therapy label includes any of the prescriptive therapy labels as described herein. A prescriptive therapy label includes a negative therapy response. A "negative therapy response," as used in this disclosure, is an indication that a prescriptive therapy should not be received by a user and/or the prescriptive therapy needs to be adjusted. For instance and without limitation, a prescriptive therapy may not be consumed by a user when a standard dose of prescriptive therapy needs to be altered, such as when a user is a hyper-metabolizer and requires a larger dose than what is commercially available and/or recommended. A prescriptive therapy may not be consumed by a user when a prescriptive therapy needs to proceed with caution to consume the prescriptive therapy and may require extra monitoring by a health care professional. A prescriptive therapy may not be consumed by a user when an alternative prescriptive therapy needs to be considered, because the user is a very poor metabolizer of the prescriptive therapy or the prescriptive therapy is contraindicated in the user because the user has a documented anaphylactic reaction to the active ingredient contained within the prescriptive therapy.

With continued reference to FIG. 1, computing device 104 is configured to identify a prescriptive therapy instruction set as a function of a prescriptive therapy label. A "prescriptive therapy instruction set," as used in this disclosure, is any instruction that details to a user how to consume a prescriptive therapy. A prescription therapy instruction set may include information such as the name of a prescriptive therapy, a recommended dose, directions as to how often a user should consume the prescriptive therapy, the duration of treatment with the prescriptive therapy, information pertaining to any titrations and/or dose adjustments that may need to occur in the future, and the like. For instance and without limitation, a prescriptive therapy instruction set may recommend a user to consume aspirin 40.5 mg once per day for sixty days for a user with a cytochrome p450 CYP2C9 mutation, that causes slowed metabolism of aspirin. In yet another non-limiting example, a prescriptive therapy instruction set may recommend a user to consume 2 grams of vancomycin every 6 hours for 14 days, for a user who is a rapid metabolizer of vancomycin.

With continued reference to FIG. 1, computing device 104 calculates a prescriptive therapy instruction by generating a prescriptive machine-learning process. A "prescriptive machine-learning process," as used in this disclosure, is a machine-learning process that utilizes a prescriptive therapy label as an input, and outputs a prescriptive therapy instruction set. Prescriptive machine-learning process includes any of the machine-learning process as described herein. For instance and without limitation, prescriptive machine-learning process may include a supervised machine-learning process, or an unsupervised machine-learning process. Prescriptive machine-learning process is trained using prescriptive training data. "Prescriptive training data," as used in this disclosure, is training data that contains a plurality of data entries containing a prescriptive therapy label element correlated with a prescriptive therapy instruction set. Prescriptive training data may be obtained from previous iterations of generating prescriptive machine-learning process, user inputs, and/or expert inputs. Computing device 104 trains prescriptive machine-learning process utilizing prescriptive training data.

With continued reference to FIG. 1, computing device 104 is configured to retrieve from a user profile database, a user specific indication for a prescriptive therapy. A "user specific indication for a prescriptive therapy," as used in this disclosure, is any problem and/or issue that a prescriptive therapy is intended to correct. A user specific indication for a prescriptive therapy may include a medical diagnosis that identifies an illness or medical condition. For instance and without limitation, a user specific indication may include a diagnosis of a medical condition such as rheumatoid arthritis. In yet another non-limiting example, a user specific indication may include a previous medical condition that resolved, such as a *c-difficile* infection. In yet another non-limiting example, a user specific indication may include a future probably medical condition, such as an increased risk of developing a medical condition such as diabetes. A user specific indication may include a nutritional deficiency, such as a deficiency of iron. A user specific indication may include an increased risk of disease, such as a genetic risk of Alzheimer's disease. A user specific indication may include a problematic behavior, such as overeating or consuming food for emotional or psychological reasons. Computing device 104 retrieves a user specific indication from user profile database and identifies a prescriptive therapy instruction set using a user specific indication.

With continued reference to FIG. 1, computing device 104 is configured to recommend a prescriptive therapy instruction set including a first prescriptive therapy. In an embodiment, computing device 104 transmits a prescriptive therapy instruction set to a remote device. In such an instance, an informed advisor such as a functional medicine doctor may review a prescriptive therapy instruction set and utilize information contained within the prescriptive therapy instruction set to generate a prescription for a user.

With continued reference to FIG. 1, computing device 104 is configured to recommend a user to not consume a first prescriptive therapy, and to recommend a second prescriptive therapy. For instance and without limitation, computing device 104 may recommend a first prescriptive therapy such as benazepril to treat a user's high blood pressure. However, a prescriptive therapy instruction set may instead recommend a second prescriptive therapy such as captopril, because the user has reduced renal function and benazepril has a long half-life and will not be easily metabolized, while captopril has a shorter half-life and will be more readily excreted by the user based on the user's renal function. In such an instance, computing device 104 recommends a prescriptive therapy instruction set containing captopril recommended at a dose of 3.125 mg every 12 hours and includes within prescriptive therapy instruction set a recommendation for the user to not consume benazepril. In yet another non-limiting example, computing device 104 recommends a user to not consume a first prescriptive therapy such as penicillin due to the user having an increased risk of developing Stevens-Johnson syndrome, and instead recommends a second prescriptive therapy such as clarithromycin.

With continued reference to FIG. 1, computing device 104 is configured to recommend a dose adjustment to a first prescriptive therapy as a function of prescriptive machine-learning process. A "dose adjustment," as used in this disclosure, is a recommended change to a measured quantity of a prescriptive therapy. For example, a dose adjustment may include changing a portion size of meal, such as by changing a large sized meal to a small sized meal. In yet another non-limiting example, a dose adjustment may include changing a standard dose of what is commercially available for any prescription and/or non-prescription medications. For instance and without limitation, an over the counter product such as acetaminophen that is available commercially as 325 mg tablets may contain a dose adjustment to instead recommend 81.25 mg once daily. In yet another non-limiting example, a dose adjustment may include changing a standard dose of fish oil that is available as 500 mg capsules to instead recommend 1500 mg twice daily. Computing device 104 is configured to generate a monitoring recommendation associated with a first prescriptive therapy. A "monitoring recommendation," as used in this disclosure, is a recommendation for clinical observation of a prescriptive therapy over time. A monitoring may include measuring one or more biological extractions to examine how a user is responding to a prescriptive therapy. For instance and without limitation, a user who starts taking atorvastatin to protect the user's memory may have a user's alanine aminotransferase (ALT) checked after three months to check for any liver damage. In yet another non-limiting example, a user who initiates a prescriptive therapy such as a low carbohydrate diet may contain a monitoring recommendation of a user's fasting blood glucose levels every month. A monitoring recommendation may include any therapeutic drug monitoring to detect and/or measure medication levels in a user's body. For instance and without limitation, a prescriptive therapy such as gentamicin may contain a monitoring recommendation to monitor blood levels of gentamicin while the user takes gentamicin so as to not cause toxicity in the blood.

With continued reference to FIG. 1, computing device 104 is configured to determine a first efficacy profile of a first prescriptive therapy. An "efficacy profile," as used in this disclosure, is an indication as to an expected response that can be achieved with a prescriptive therapy for a given user. An efficacy profile may include one or more phenotypes that may affect the efficacy of a prescriptive therapy for a user. For instance and without limitation, for a given prescriptive therapy, a user may be a poor metabolizer, indicating that a prescriptive therapy has none to very low activity within the user's body, and that a prescriptive therapy that is converted to an active metabolite may have reduced activity, while active prescriptive therapies that are converted to inactive metabolites may cause side effects and/or toxicity An efficacy profile may indicate that a user is an intermediate metabolizer and that a prescriptive therapy that is consumed by an intermediate metabolizer may still have decreased activity, and prescriptive therapies that are converted to active metabolites may have reduced efficacy, while active prescriptive therapies that are converted to inactive metabolites may cause side effects or toxicity. An efficacy profile may indicate that a user is a normal metabolizer and has a normal level of activity, where prescriptive therapies are metabolized at a normal rate. An efficacy profile may indicate that a user is a rapid metabolizer, and that a prescriptive therapy may have increased activity within the user's body, and prescriptive therapies that are converted to active metabolites may cause side effects and/or toxicity while active prescriptive therapies that are converted to inactive metabolites may lack efficacy. An efficacy profile may indicate that a user is an ultra-rapid metabolizer, and that a prescriptive therapy may have increased activity, and prescriptive therapies that are converted to active metabolites may cause side effects and/or toxicity, and active prescriptive therapies that are converted to inactive metabolites may lack efficacy. Computing device 104 identifies a second prescriptive therapy containing a second efficacy profile and recommends the second prescriptive therapy as a function of the second efficacy profile. For instance and without limitation, computing device 104 determines a first efficacy profile of a first prescriptive therapy to be indicate that a user is a poor metabolizer of a first prescriptive therapy, so computing device 104 identifies a second prescriptive therapy containing a second efficacy profile that indicates the second prescriptive therapy has a second efficacy profile that indicates the user is a normal metabolizer, and as such, computing device 104 recommends the second prescriptive therapy as a function of the second efficacy profile. Information pertaining to an efficacy profile may be stored within user profile database. Computing device 104 may recommend a second prescriptive therapy containing a second efficacy profile as compared to a first prescriptive therapy having a first efficacy profile when the first prescriptive therapy is related to the second prescriptive therapy. A first prescriptive therapy is related to a second prescriptive therapy when the first prescriptive therapy and the second prescriptive therapy are both used for a common purpose. A common purpose may include when prescriptive therapies may be utilized to treat the same user specific indication or when prescriptive therapies belong to the same drug class. For instance and without limitation, a first prescriptive therapy may include a prescription drug such as penicillin, and a second prescriptive therapy may include a prescription drug such as cephalosporin, where penicillin and cephalosporin both share a common purpose of belonging to the drug class of being beta-lactam antibiotics. In yet another non-limiting example, a first prescriptive therapy may include a recommended food such as broccoli, while a second prescriptive therapy may include a food such as Brussel sprouts, where broccoli and Brussel sprouts share a common purpose of both being cruciferous vegetables. Computing device 104 is configured to identify a first prescriptive therapy companion. A "prescriptive therapy companion," as used in this disclosure, is any prescriptive therapy that is recommended to be administered in combination with a first prescriptive therapy. A prescriptive therapy may be recommended to be administered in combination with a first prescriptive therapy when a first prescriptive therapy may cause the depletion and/or elimination of various nutrients. For instance and without limitation, a first prescriptive therapy containing zinc may be recommended to be administered in combination with a prescriptive therapy companion such as copper, because zinc administration can lead to long term copper deficiency. In yet another non-limiting example, a first prescriptive therapy such as an antibiotic such as azithromycin may be recommended to be administered in combination with a prescriptive therapy companion such as a probiotic supplement containing a strain of *Saccharomyces Boulardii*, as the probiotic supplement will not be killed off by the azithromycin, and will help guard against other infections including for example, *C-difficile* diarrhea. Computing device 104 locates a second prescriptive therapy as a function of a first prescriptive therapy companion and recommends administration of the first prescriptive therapy and the second prescriptive therapy.

Figure 2:
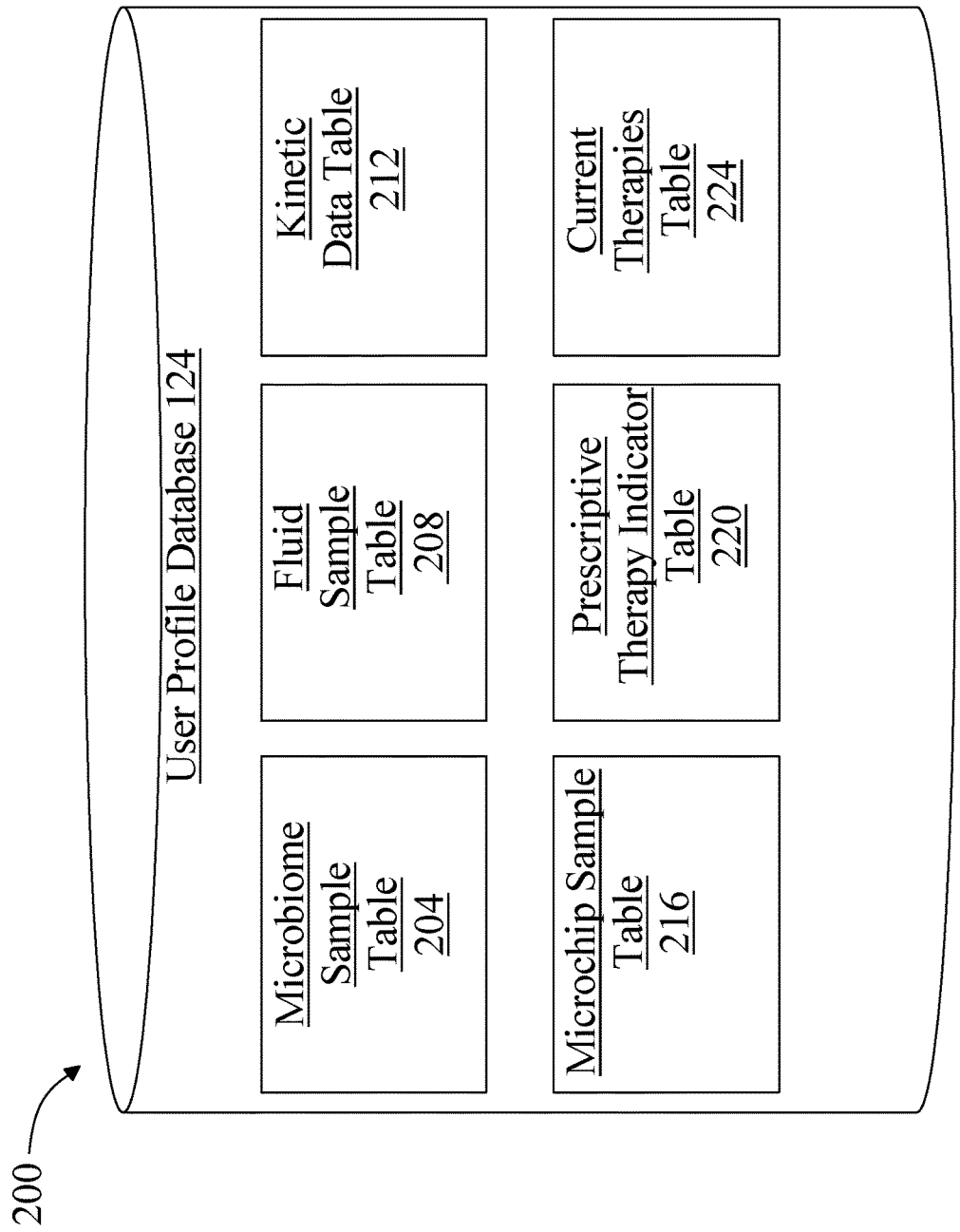
FIG. 2 is a block diagram illustrating an exemplary embodiment of a user profile database.

Referring now to FIG. 2, an exemplary embodiment 200 of user profile database 124 is illustrated. User profile database 124 may be implemented as any data structure as described above in reference to FIG. 1. One or more tables contained within user profile database 124 may include microbiome sample table 204; microbiome sample table 204 may include one or more biological extraction 116 relating to the microbiome. For instance and without limitation, microbiome sample table 204 may include a physically extracted sample such as a stool sample analyzed for the presence of pathogenic species such as parasites and anaerobes. One or more tables contained within user profile database 124 may include fluid sample table 208; fluid sample table 208 may include one or more biological extraction 116 containing fluid samples. For instance and without limitation, fluid sample table 208 may include a urine sample analyzed for the presence or absence of glucose. One or more tables contained within user profile database 124 may include intracellular kinetic data table 212; kinetic data table 212 may include one or more elements of user kinetic data. For instance and without limitation, kinetic data table 212 may include data describing a user's hepatic and renal function. One or more tables contained within user profile database 124 may include microchip sample table 216; microchip sample table 216 may include one or more biological extraction 116 obtained from a microchip. For instance and without limitation, microchip sample table 216 may include a blood sugar level obtained from a microchip embedded under a user's skin. One or more tables contained within user profile database 124 may include prescriptive therapy indicator table 220; prescriptive therapy indicator table 220 may include one or more prescriptive therapy indicators pertaining to a user. For instance and without limitation, prescriptive therapy indicator table 220 may include information pertaining to a user's cultural background, age, sex, marital status, occupation, and the like. One or more tables contained within user profile database 124 may include current therapies table 224; current therapies table 224 may include one or more current therapies the user is on and/or one or more medical conditions or preexisting conditions the user may have been diagnosed with. For instance and without limitation, current therapies table 224 may include a list of one or more prescriptive or non-prescriptive therapies the user is currently taking which includes atorvastatin, fish oil, coenzyme q-10, lisinopril, and a daily aspirin.

Figure 3:
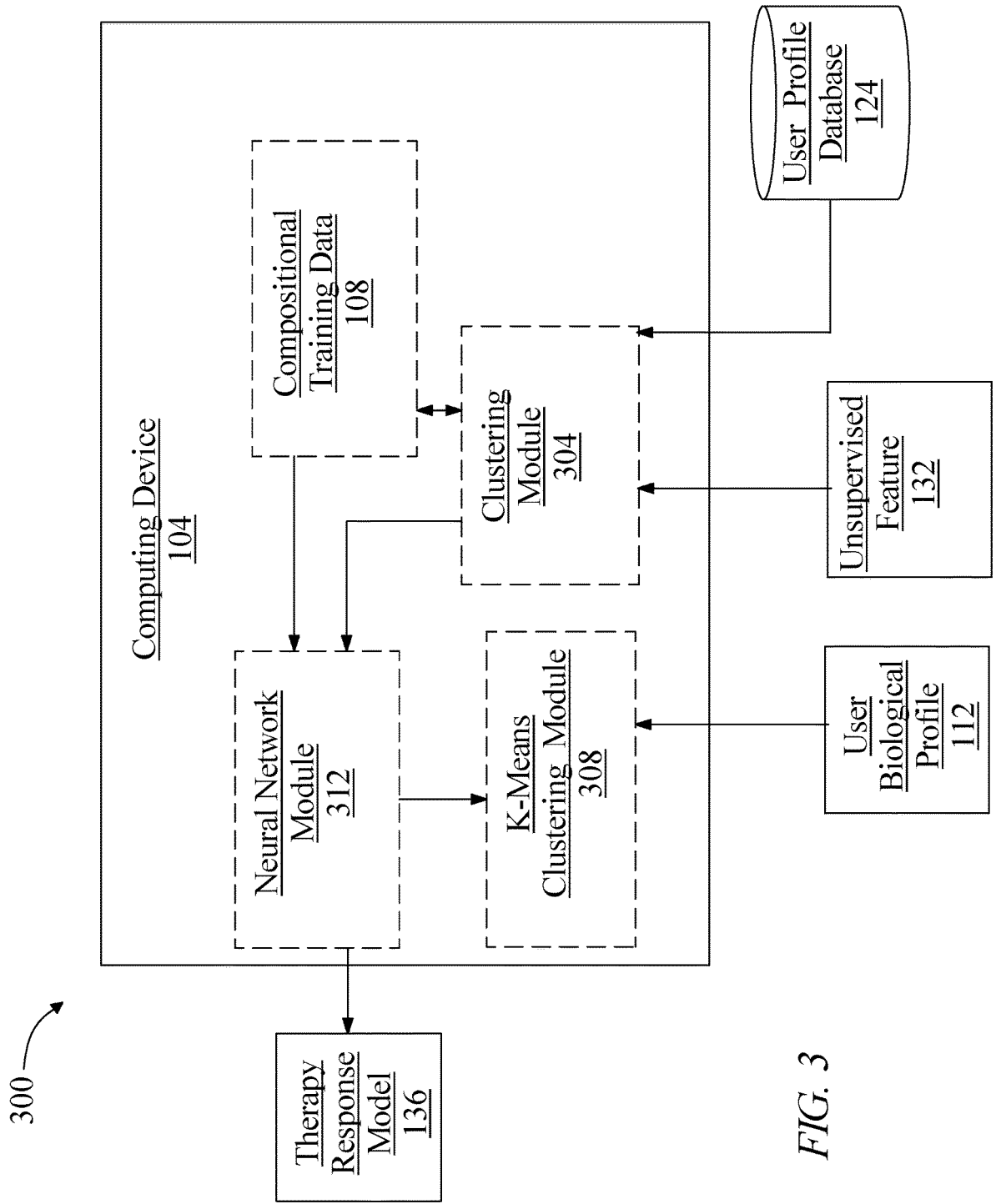
FIG. 3 is a block diagram of unsupervised machine-learning models.

Referring now to FIG. 3, an exemplary embodiment of unsupervised machine-learning algorithms is illustrated. Computing device 104 receives compositional training data 108. Compositional training data 108 includes a plurality of unclassified data entries as described above in more detail in reference to FIG. 1. Computing device 104 generates an unsupervised machine-learning algorithm utilizing a biological profile as an input and outputting a therapy response model 136. Therapy response model 136 includes any of the therapy response model 136 as described above in reference to FIG. 1. Computing device 104 may include one or more unsupervised machine-learning modules. Unsupervised machine-learning modules may be implemented as any hardware and/or software module. Unsupervised machine-learning modules may perform one or more unsupervised machine-learning algorithms. One or more unsupervised machine-learning modules may include clustering module 304. Clustering module 304 may generate one or more clustering algorithms. One or more unsupervised machine-learning modules may include k-means clustering module 308. K-means clustering module 308 may perform one or more k-means clustering algorithms. One or more unsupervised machine-learning modules may include neural network module 312. Neural network module 312 may perform one or more neural networks. Computing device 104 may include one or more unsupervised machine-learning modules not illustrated. For example, computing device 104 may include k-nearest neighbor module, hierarchical clustering module, deep belief net module, Hebbian learning module, DBSCAN module, OPTICS module and the like. One or more unsupervised machine-learning algorithms may be optimized using one or more unsupervised feature 132. Unsupervised feature 132 include any of the unsupervised feature 132 as described above. In an embodiment, an unsupervised feature 132 may be selected to match one or more prescriptive therapy indicators contained within user profile database 124. For instance and without limitation, a prescriptive therapy indicator contained within user profile database 124 that indicates a user has a polymorphism of one or more drug metabolizing enzymes may be utilized to select a prescriptive factor that contains the same polymorphism of the one or more drug metabolizing enzymes.

Referring now to FIG. 4, an exemplary embodiment of unsupervised feature 132 are illustrated. Unsupervised feature 132 include any of the unsupervised feature 132 as described above in reference to FIG. 1. Unsupervised feature 132 may be categorized into one or more categories including genetic features 404, constitutional features 408, and ecological features 412. Genetic features 404 are one or more facets relating to genetic matter that may be utilized to generate an unsupervised machine-learning algorithm. Genetic features 404 include absorption, distribution, metabolism, excretion, body weight, genetic conditions, genetic polymorphism of drug metabolizing enzymes, height, race, receptor sensitivity and sex. Constitutional features 408 are one or more facets relating to the biology of the human body utilized to generate an unsupervised machine-learning algorithm. Constitutional features 408 include absorption, distribution, metabolism, excretion, age, alcohol use, body weight, cardiovascular function, diet, diseases, co-morbid conditions, height, kidney function, liver function, receptor sensitivity, smoking, and stress. Ecological features 412 include one or more facets relating to the environment that may be utilized to generate an unsupervised machine-learning algorithm. Ecological features 412 may include for example alcohol use, climate, culture, educational status, language, socioeconomic factors, profession, diet, diseases, co-morbid conditions, drug adherence, medical practices, pollution, smoking, stress, sunlight exposure, and therapeutic approach.

Figure 5A:
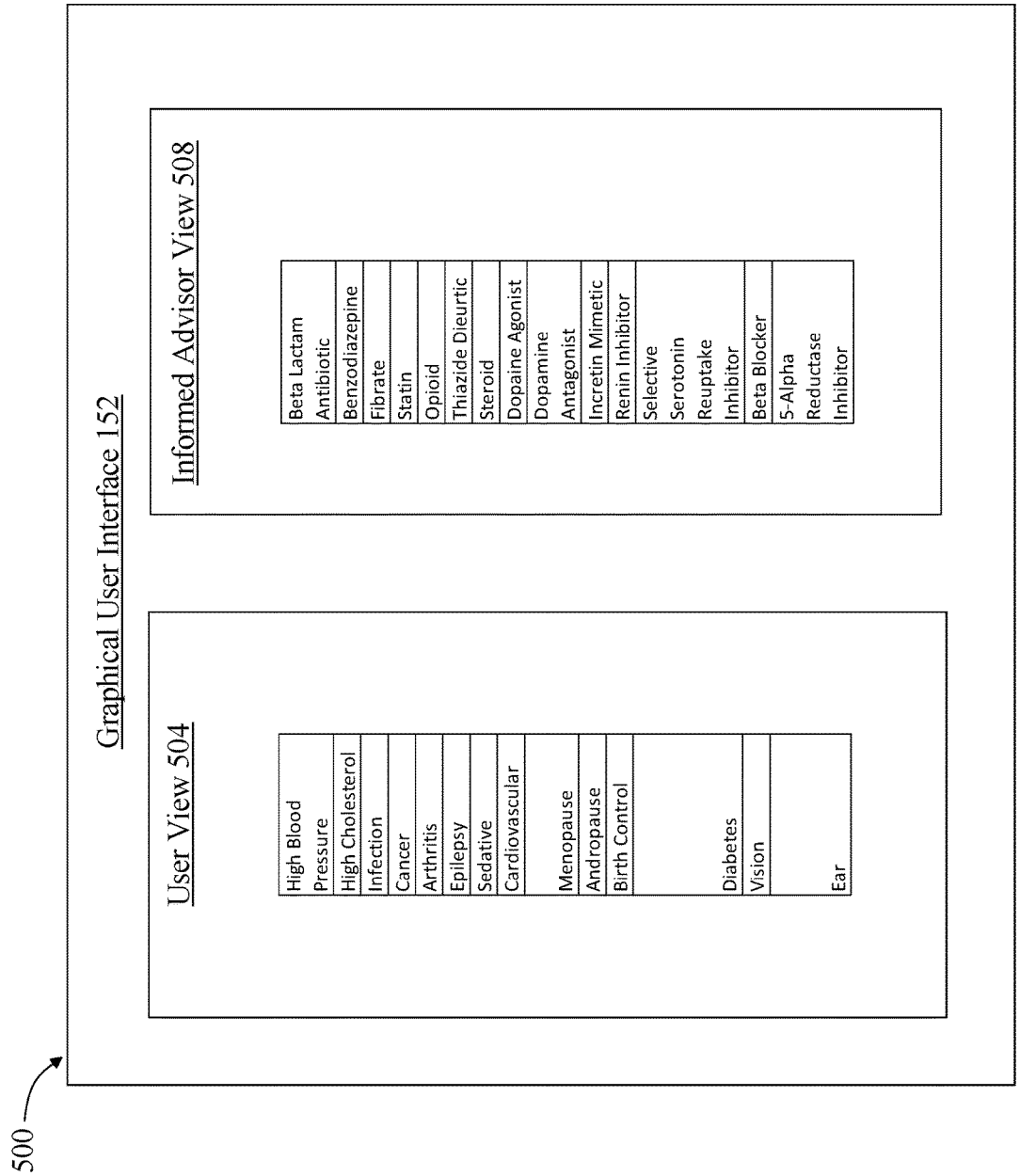
FIGS. 5A-B are diagrammatic representations of graphical user interface.
Figure 5B:
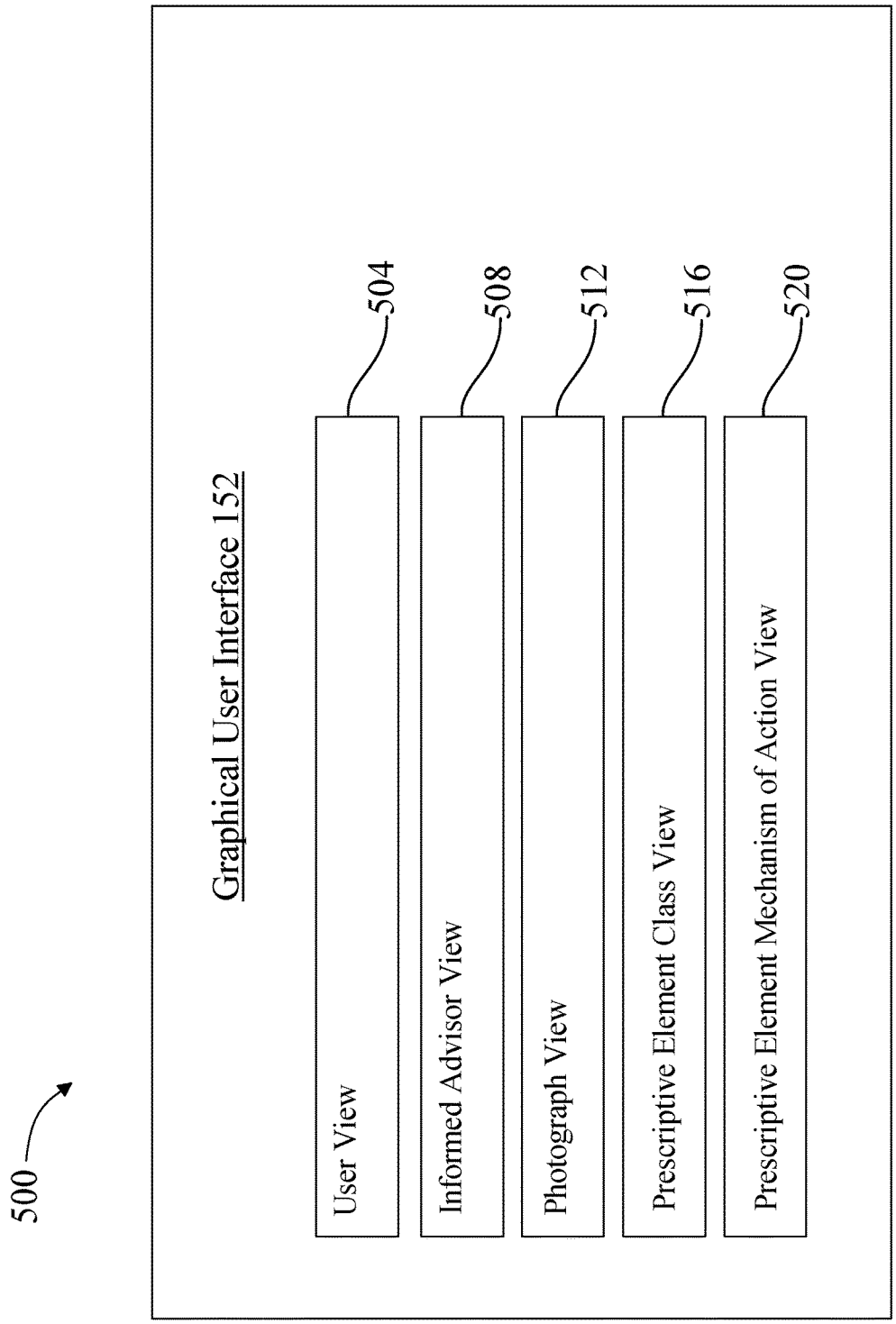

Referring now to FIGS. 5A-5B, an exemplary embodiment 500 of graphical user interface 152 is illustrated. FIG. 5A illustrates an exemplary embodiment of user view 504 and informed advisor view 508. User view 504 may display one or more prescriptive therapies by condition or diagnosis that the prescriptive therapy may treat such as high blood pressure, high cholesterol, infection, cancer, arthritis, epilepsy, sedative, cardiovascular, menopause, andropause, birth control, diabetes, vision, and ear. In an embodiment, user view 504 may list one or more affected parts of the body such as vision or ear. In an embodiment, a user may select one or more conditions to display more information that includes one or more prescriptive therapies that may be utilized to treat the selected condition or diagnosis. Informed advisor view 508 may display one or more prescriptive therapies by drug class, active ingredient, chemical structure, and/or mechanism of action. Informed advisor view 508 may list one or more prescriptive therapy by drug class, active ingredient, chemical structure, and/or mechanism of action which may include beta lactam antibiotic, benzodiazepine, fibrate, statin, opioid, thiazide diuretic, steroid, dopamine agonist, dopamine antagonist, incretin mimetic, renin inhibitor, selective serotonin reuptake inhibitor, beta blocker, and 5-alpha reductase inhibitor. Referring now to FIG. 5B, an exemplary embodiment of a view selection of graphical user interface 152 is illustrated. In an embodiment, a user may select what type of view they would like information to be displayed on graphical user interface 152. View choices may include user view 504 which may include any of the views as described above. View choice may include informed advisor view 508 which may include any of the views as described above. View choice may include photograph view 512 which may include displaying one or more prescriptive therapies as a photograph. View choice may include prescriptive therapy class view 516, which may display one or more classes of prescriptive therapies. View choice may include prescriptive therapy mechanism of action view 520 which may display one or more prescriptive therapies categorized according to mechanism of action.

Figure 6:
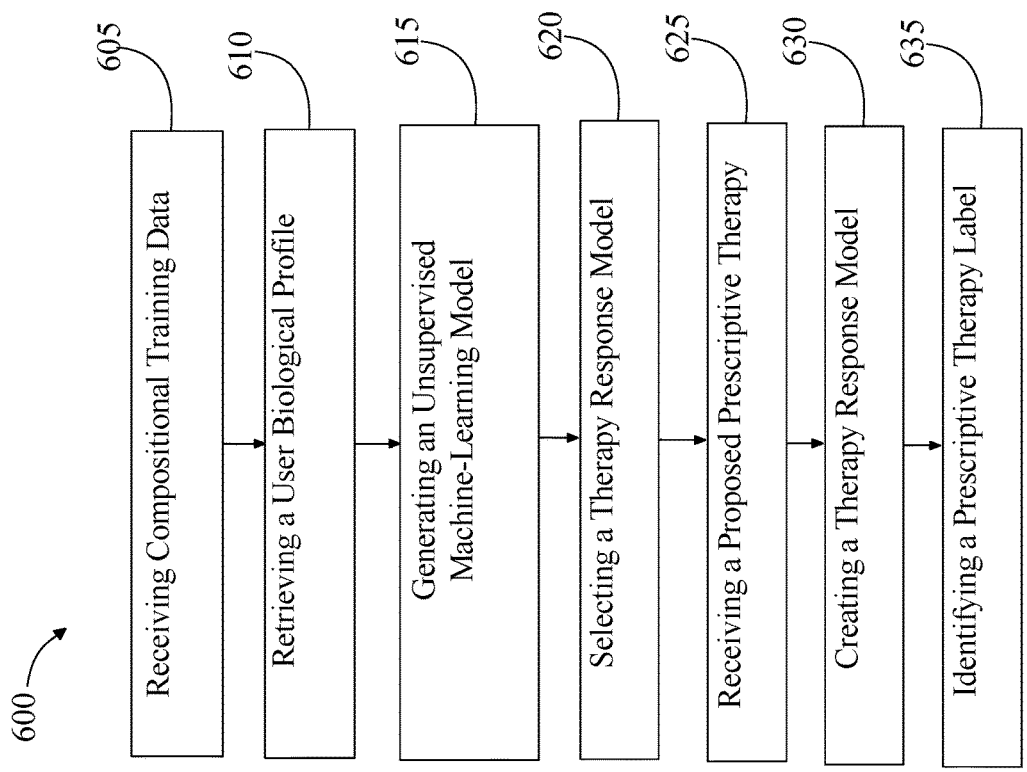
FIG. 6 is a process flow diagram illustrating an exemplary embodiment of a method of informed selection of prescriptive therapies.

Referring now to FIG. 6, an exemplary embodiment of a method 600 of informed selection of prescriptive therapies is illustrated. At step 605 a computing device receives compositional training data 108. Compositional training data 108 includes any of the compositional training data 108 as described above in reference to FIG. 1. Compositional training data 108 includes a plurality of unclassified data entries. Compositional training data 108 and/or elements thereof may be entered by one or more users including for example by one or more experts from remote device 144 and/or from graphical user interface 152. Experts may include one or more physicians, medical experts, nurses, experts in a particular topic and the like who may hold one or more credentials that may certify them as an expert. Credentials may include one or more licenses such as a medical license or a license to practice in a particular field of medicine such as a license to prescribe controlled substances. Credentials may include one or more board certifications such as aa certified personal trainer, a certified group exercise instructor, a certified board expert in gastroenterology, a certified medical exercise specialist, a certification from an organization relating to functional medicine such as the American Academy of Anti-Aging Medicine and the like. Credentials may include a particular field of experience and practice such as a functional medicines physician, a rheumatologist, psychiatrist, and the like. Credentials may include publications in top leading medical journals, newspapers, and articles. Credentials may include participation in one or more clinical trials.

With continued reference to FIG. 6, at step 610 computing device 104 retrieves a user biological profile 112. User biological profile 112 includes any of the user biological profile 112 as described above in reference to FIG. 1. User biological profile 112 includes a biological extraction 116 and a prescriptive therapy indicator. Biological extraction 116 includes any of the biological extraction 116 as described above in reference to FIG. 1. For instance and without limitation, a biological extraction 116 may include one or more hormone levels obtained from a microchip implanted in a user's skin. In yet another non-limiting example, a biological extraction 116 may include a stool sample analyzed for one or more bacterial strains such as *Clostridium difficile*, *Vibrio cholerae*, *Escherichia coli*, *Staphylococcus aureus*, *Vibrio Parahaemolyticus*, *Giardia lamblia*, and *Strongyloides stercoralis*. Prescriptive therapy indicators include one or more factors that may affect the administration and/or metabolism of one or more prescriptive therapies. For instance and without limitation, a genetic prescriptive therapy indicator may include a phenotype of cytochrome P450 enzymes such as CYP2C9*2 and CYP2C9*3 that result in reduced enzymatic activity and exhibition of reduced warfarin clearance. In such an instance, persons exhibiting such phenotypes may require lower doses of warfarin as compared to those who do not exhibit those phenotypes as they otherwise are at risk of excessive anticoagulation. In yet another non-limiting example a prescriptive therapy indicator may include an ecological feature such as a person's race and cultural background. For example, a person of African American race exhibits a different pathophysiology of hypertension as compared to a person of the Caucasian race. In yet another non-limiting example, a prescriptive therapy indicator may include a constitutional feature such as a person's body weight. For example, a person who is extremely overweight and considered obese may require a much higher dose of a medication as compared to a person who has a very low body mass index (BMI) and may be considered underweight or of normal weight.

With continued reference to FIG. 6, at step 615 a computing device generates an unsupervised machine-learning model 128 using compositional training data 108. Unsupervised machine-learning model includes any of the unsupervised machine-learning model 128 as described above in reference to FIGS. 1-5. Unsupervised machine-learning model utilizes a biological profile as an input and outputs a therapy response label. A "therapy response label," as used in this disclosure, is a text handle containing a string of characters that labels an output generated by an unsupervised machine-learning model. For instance and without limitation, therapy response label may describe the contents of a cluster produced by a clustering algorithm. In an embodiment, contents of data entries contained within a cluster label may be utilized to generate a training set that may be utilized to generate a therapy response model. For instance and without limitation, data entries contained within data cluster that share an attribute such as the same demographics and same co-morbid disease states may be utilized as training data to generate therapy response model. Therapy response label may be utilized to select a therapy response model. For example, a therapy response label that indicates a shared feature of data entries contained within a cluster such as the same age as the user may be utilized to select a therapy response model generated for users of the same age. Unsupervised machine-learning model 128 may include generating one or more unsupervised machine-learning algorithms such as for example, clustering algorithms including hierarchical clustering, k-means clustering, mixture models, DBSCAN, OPTICS algorithm, anomaly detection such as local outlier factor, neural networks such as autoencoders, deep belief nets, Hebbian learning, generative adversarial networks, and self-organizing maps.

With continued reference to FIG. 6, generating an unsupervised machine-learning algorithm includes selecting an unsupervised feature 132 utilizing a user biological profile 112. Unsupervised feature 132 includes a trait or characteristic that is utilized to select and/or generate an unsupervised machine learning algorithm. Computing device 104 may select an unsupervised feature 132 that matches a prescriptive therapy treatment indicator contained within a user profile database 124. For instance and without limitation, a prescriptive therapy treatment indicator contained within user profile database 124 that indicates a user has a genetic polymorphism to one or more prescriptive therapies may be utilized to select an unsupervised feature 132 containing the same genetic polymorphism. In yet another non-limiting example, a prescriptive therapy treatment indicator such as a user's educational status may be utilized to select an unsupervised feature 132 that matches the user's educational status. An unsupervised feature 132 may include one or more genetic features. For example, an unsupervised feature 132 may include a polymorphism to cytochrome p450 2D6 containing CYP2D6*6 phenotype indicating a person who is a poor metabolizer of prescriptive therapies through the CYP2D6 cytochromes, thereby necessitating the need for higher doses of prescriptive therapies metabolized through the cytochrome such as codeine as persons with this phenotype exhibit poor conversion of codeine to morphine and as such exhibit poor analgesic responses. An unsupervised feature 132 may include one or more constitutional features. For example, an unsupervised feature 132 may include one or more measurements of a receptor response to one or more prescriptive therapies. For instance and without limitation, a person with impaired serotonin receptors may not response to a prescriptive therapy such as a selective serotonin reuptake inhibitor (SSRI) but may exhibit a response to a prescriptive therapy that does not work on serotonin receptors such as bupropion. An unsupervised feature 132 may include one or more ecological features. For example, an unsupervised feature 132 may include one or more measurements of a user's environment which may indicate that based on a user's water supply at home user has lead poisoning which may concomitantly alter user's response to one or more prescriptive therapies. Unsupervised feature 132 may include but are not limited to any of the unsupervised feature 132 as described above in reference to FIG. 4.

With continued reference to FIG. 6, at step 620 a computing device 104 selects a therapy response model 136 as a function of generating an unsupervised machine-learning model 128. Therapy response model 136 includes any of the therapy response model 136 as described above in reference to FIGS. 1-5. Computing device 104 may select a therapy response model 136 utilizing one or more unsupervised feature 132. For example, an unsupervised feature 132 that indicates a user is of Native American background and smokes peyote as part of customary cultural traditions may cause computing device 104 to select a therapy response model 136 that matches and/or closely resembles such unsupervised feature 132. In yet another non-limiting example, an unsupervised feature 132 that indicates a user is of European descent, doesn't consume alcohol, and is an ultra-rapid metabolizer of caffeine containing ingredients may cause computing device 104 to select a therapy response model 136 that matches and/or closely resembles such unsupervised feature 132.

With continued reference to FIG. 6, at step 625 computing device 104 receives from a remote device 144 a proposed prescriptive therapy 148. Proposed prescriptive therapy 148 includes one or more prescriptive therapies that are being considered as possible treatment options for a user. Computing device 104 may receive a proposed prescriptive therapy 148 from remote device 144 utilizing any network methodology as described herein. Proposed prescriptive therapy 148 may be generated by a user on user's remote device 144 such as when a user has been recently diagnosed with a new medical condition and user is curious as to different possible treatments user may need to take. In yet another non-limiting example, proposed prescriptive therapy 148 may be generated by a user after user experiences an unwanted side effect from a prescriptive therapy user is currently taking and user seeks to determine what other prescriptive therapies user may be able to take to discuss with user's doctor at an upcoming appointment. Proposed prescriptive therapy 148 may be generated by an informed advisor from a remote device 144, such as when an informed advisor is considering a new treatment option for a user. Proposed prescriptive therapy 148 may be input by a user or informed advisor on graphical user interface 152 located on processor. Proposed prescriptive therapy may include a description of one or more medications, drug classes, disease states that need to be treated and the like as described above in more detail.

With continued reference to FIG. 6, at step 630 computing device 104 creates a therapy response model 136 utilizing a selected therapy response model 136. Therapy response model 136 relates a biological profile to prescriptive therapy label 140. Therapy response model 136 may include any of the therapy response model 136 as described above in reference to FIGS. 1-5. Therapy response model 136 may include calculating one or more machine-learning algorithms. Machine-learning algorithms may include any of the machine-learning algorithms as described above in reference to FIGS. 1-5. Machine-learning algorithms may include one or more supervised machine-learning algorithms, one or more unsupervised machine-learning algorithms, one or more lazy learning algorithms, and the like.

With continued reference to FIG. 6, at step 635 computing device 104 identifies a prescriptive therapy label 140 for a proposed prescriptive therapy 148. Prescriptive therapy label 140 may indicate whether a proposed prescriptive therapy 148 will be tolerated or not tolerated by a user. Prescriptive therapy label 140 may indicate whether a class of prescriptive therapies such as beta lactam antibiotics will be tolerated or not tolerated by a user. In an embodiment, prescriptive therapy label 140 may indicate whether certain members of a class of prescriptive therapies will be tolerated. For example, a prescriptive therapy label 140 may indicate that selective serotonin reuptake inhibits such as fluoxetine and duloxetine will not be tolerated by a user, but that venlafaxine and citalopram will be tolerated by the user. Prescriptive therapy label may indicate that aminoglycosides and clindamycin will not be tolerated by a user but daptomycin, fluoroquinolones, and carbapenems will be tolerated by the user. Prescriptive therapy label 140 may indicate one or more prescriptive therapies that can be used in lieu of one or more prescriptive therapies that are not compatible with the user. For example, a prescriptive therapy label 140 may indicate that all thiazide diuretics will not be compatible with a user but an ace-inhibitor such as lisinopril will be tolerated by the user as well as a calcium channel blocker such as amlodipine. Prescriptive therapy label 140 may indicate one or more ideal doses of a prescriptive therapy for a label, as well as one or more sets of instructions indicating how frequently a user should consume a prescriptive therapy, such as once per day, every other day, once per week and the like.

With continued reference to FIG. 6, identifying a prescriptive therapy label 140 includes receiving contraindication training data 156 wherein the contraindication training data 156 contains a plurality of data entries containing prescriptive therapies and correlated contraindications 160. Contraindications 160 include any of the contraindications 160 as described above in reference to FIGS. 1-5. Computing device 104 retrieves user current therapies 164 such as from user profile database 124. Current therapies 164 may include one or more medications the user may be currently consuming as described above. Current therapies 164 may include one or more current and/or preexisting medical conditions the user may have been diagnosed with such as multiple sclerosis or chronic fatigue syndrome. Computing device 104 generates a machine-learning algorithm using the contraindication training data 156 wherein the machine-learning algorithm utilizes prescriptive therapies as an input and outputs contraindications 160. Machine-learning algorithm includes any of the machine-learning algorithms as described above in reference to FIGS. 1-5. Computing device 104 evaluates the output contraindications 160. Computing device 104 may evaluate output contraindications 160 utilizing any of the methodologies as described above in reference to FIGS. 1-5. For instance and without limitation, computing device 104 may determine if a proposed prescriptive therapy 148 matches any of the output contraindications. In such an instance, where a proposed prescriptive therapy 148 matches an output contraindication computing device 104 may generate a prescriptive therapy label 140 that indicates that the proposed prescriptive therapy 148 is not compatible with the user. In an embodiment, where proposed prescriptive therapy 148 does not match any of the output contraindications 160, computing device 104 generate a prescriptive therapy label 140 that indicates that the proposed prescriptive therapy 148 is compatible with the user.

With continued reference to FIG. 6, identifying a prescriptive therapy label 140 includes receiving kinetic training data 168 wherein the kinetic training data 168 contains a plurality of data entries containing kinetic data and correlated prescriptive therapies. Kinetic training data 168 includes any of the kinetic training data 168 as described above in reference to FIGS. 1-5. Computing device 104 retrieves an element of user kinetic data such as from user profile database 124. Kinetic data includes an element of data describing how a body processes a prescriptive therapy. For instance and without limitation, kinetic data may describe a user's altered renal metabolism, or a user's leaky gut syndrome which causes user to have altered oral gastrointestinal absorption. Computing device 104 generates a machine-learning algorithm using the kinetic training data 168 wherein the machine-learning algorithm utilizes the element of user kinetic data as an input and outputs compatible prescriptive therapies 172. Machine-learning algorithm includes any of the machine-learning algorithms as described above in reference to FIGS. 1-5. Computing device 104 compares output compatible prescriptive therapies 172 to proposed prescriptive therapy 148. In an embodiment, computing device 104 may identify a prescriptive therapy label 140 that indicates a prescriptive therapy is compatible with a user if a proposed prescriptive therapy 148 matches an output compatible prescriptive therapy. Computing device 104 may identify a prescriptive therapy label 140 that indicates a prescriptive therapy is not compatible with a user if a proposed prescriptive therapy 148 does not match an output compatible prescriptive therapy.

With continued reference to FIG. 6, identifying a prescriptive therapy label 140 includes receiving genetic training data 176 wherein the genetic training data 176 contains a plurality of data entries containing genetic data and correlated prescriptive therapies. Genetic data includes any of the genetic data as described above in reference to FIGS. 1-5. Computing device 104 retrieves an element of user genetic data 180. An element of user genetic data 180 includes any of the user genetic data 180 as described above in reference to FIGS. 1-5. Computing device 104 may retrieve an element of user data from user profile database 124. Computing device 104 generates a machine-learning algorithm using the genetic training data 176 wherein the machine-learning algorithm utilizes the element of user genetic data 180 as an input and outputs compatible prescriptive therapies 172. Computing device 104 identifies a prescriptive therapy label 140 as a function of generating the machine-learning algorithm. For instance and without limitation, computing device 104 may identify a prescriptive therapy label 140 as compatible for a proposed prescriptive therapy 148 that matches an output compatible prescriptive therapy. Computing device 104 may identify a prescriptive therapy label 140 as incompatible for a proposed prescriptive therapy 148 that does not match an output compatible prescriptive therapy.

Figure 7:
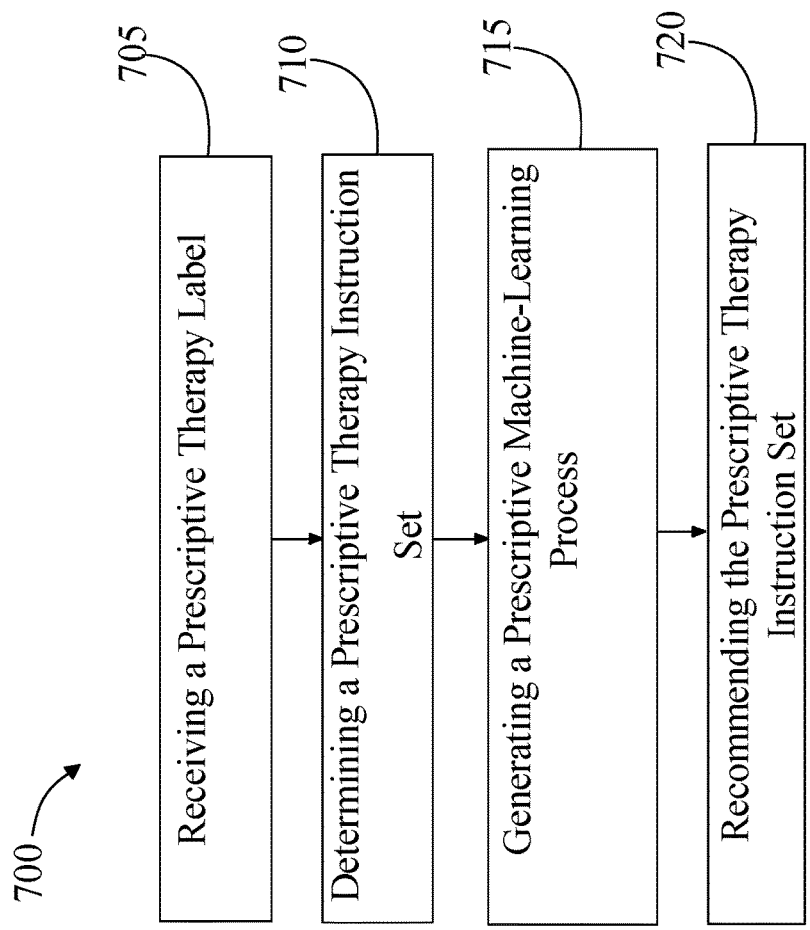
FIG. 7 is a process flow diagram illustrating an exemplary embodiment of informed selection of prescriptive therapies.

Referring now to FIG. 7, an exemplary embodiment of a method 700 of informed selection of prescriptive therapies is illustrated. At step 705, computing device 104 receives a prescriptive therapy label. A prescriptive therapy label includes any of the prescriptive therapy label as described above in more detail in reference to FIGS. 1-6. A prescriptive therapy label may include a negative therapy response. A negative therapy response includes any of the negative therapy responses as described above in more detail in reference to FIG. 1. A negative therapy response may include an indication that a prescriptive therapy should not be consumed by a user and/or the prescriptive therapy needs to be adjusted. For instance and without limitation, a negative therapy response may include an indication that a standard dose of a medication such as azithromycin may need to adjust for a user, because the user has impaired function of Cytochrome P4503A4, and as such has altered metabolism of azithromycin. A prescriptive therapy label may include a positive therapy response, which includes an indication that a prescriptive therapy can be consumed by a user and/or the prescriptive therapy does not need to be adjusted. For instance and without limitation, a positive therapy response may indicate that a standard commercially available dose of the anti-depressant such as fluoxetine, can be consumed by the user.

With continued reference to FIG. 7, at step 710, computing device 104 determines a prescriptive therapy instruction set as a function of a prescriptive therapy label. A prescriptive therapy instruction set includes any of the prescriptive therapy instruction sets as described above in more detail in reference to FIG. 1. A prescriptive therapy instruction set contains one or more recommended prescriptive therapies along with a recommended dose, duration, and/or instructions as to how a user should consume a prescriptive therapy and for how long. For instance and without limitation, a prescriptive therapy instruction set may recommend a user to consume a prescriptive therapy such as a collagen smoothie containing a minimum of 500 mg of collagen every morning for a minimum of six weeks. In yet another non-limiting example, a prescriptive therapy instruction set may recommend a user to consume a medication such as prednisone at 5 mg three times daily for one week, then 5 mg twice daily for one week, and 5 mg once daily for one week and then to stop all subsequent doses of prednisone.

With continued reference to FIG. 7, at step 715, computing device 104 generates a prescriptive machine-learning process. A prescriptive machine-learning process includes any of the machine-learning processes as described above in more detail in reference to FIG. 1. Computing device 104 trains prescriptive machine-learning process using prescriptive training data. Prescriptive training data includes any of the prescriptive training data as described above in more detail in reference to FIG. 1. Prescriptive training data contains a plurality of data entries containing a prescriptive therapy label element correlated with a prescriptive therapy instruction set. Computing device 104 identifies a prescriptive instruction set as a function of generating a prescriptive machine-learning process.

With continued reference to FIG. 7, at step 720, computing device 104 recommends a prescriptive therapy instruction set including a first prescriptive therapy. A prescriptive instruction set includes any of the prescriptive instruction sets as described herein. Computing device 104 generates a prescriptive instruction set by retrieving from a user profile database, a user specific indication for a prescriptive therapy. A user specific indication for a prescriptive therapy includes any of the user specific indications for a prescriptive therapy as described above in more detail in reference to FIG. 1. For example, a user specific indication may include a diagnosis of a medical condition, such as hypertension. In yet another non-limiting example, a user specific indication may include a risk factor for developing a medical condition in the future such as an increased risk of macular degeneration. In yet another non-limiting example, a user specific indication may include a previous medical condition and/or diagnosis that has resolved, been treated, entered remission, subsided and the like. For example, a user specific indication may indicate that a user was diagnosed with ulcerative colitis, and had a flare three years prior, but the user is currently in remission from the ulcerative colitis. Computing device 104 utilizes a user specific indication to identify a prescriptive therapy instruction set. For example, a prescriptive therapy instruction set that contains a prescriptive therapy such as aspirin to be taken daily to reduce the user's risk of heart attack, may utilize a user specific indication of a previous heart attack to recommend a dose contained within a prescriptive therapy instruction set that contains 300 mg of aspirin once daily.

With continued reference to FIG. 7, computing device 104 recommends a prescriptive therapy instruction set by evaluating a plurality of prescriptive therapies. Computing device 104 recommends a user not to consume a prescriptive therapy, such as when the prescriptive therapy may have altered metabolism within the user's body and may put the user at high risk of experiencing toxic side effects. Computing device 104 locates a second prescriptive therapy that will have standard metabolism within the user's body and recommends the second prescriptive therapy within the prescriptive instruction set. Computing device 104 recommends a prescriptive therapy instruction set by recommending a dose adjustment to a first prescriptive therapy as a function of a prescriptive machine-learning process. A dose adjustment includes any of the dose adjustments as described above in more detail in reference to FIG. 1. A dose adjustment may include a change in dose as to what may be commercially available for a drug, medication, and/or supplement, or a dose adjustment may include a change in serving size for a food or meal. For instance and without limitation, computing device 104 may recommend a dose adjustment for a first prescriptive therapy such as levothyroxine, which is commercially available in various dosages ranging from 25 mcg up to 300 mcg. In such an instance, computing device 104 may recommend a dose adjustment for levothyroxine so as to recommend a user take 12 mcg as compared to commercially available 25 mcg dose. In yet another non-limiting example, computing device 104 may recommend a dose adjustment for a first prescriptive therapy such as a vegan entrée, which is usually served in a large portion and instead to recommend that the user consume the small size portion, as the large size portion has too many grams of sugar for the user to properly metabolize. Computing device 104 generates a monitoring recommendation associated with a first prescriptive therapy. A monitoring recommendation includes any of the monitoring recommendations as described above in more detail in reference to FIG. 1. A monitoring recommendation may include one or more suggested biological extractions that may need to be monitored in conjunction with a prescriptive therapy. For example, a prescriptive therapy such as consuming a vegan diet may contain a monitoring recommendation for a user to have blood levels of Vitamin B12, iron, ferritin, calcium, and Vitamin D.

With continued reference to FIG. 7, computing device 104 is configured to recommend a prescriptive therapy instruction set by determining a first efficacy profile of a first prescriptive therapy. An efficacy profile contains an indication as to an expected response that can be achieved with a prescriptive therapy. For instance and without limitation, an efficacy profile may indicate that a user is a rapid metabolizer of a first prescriptive therapy. In yet another non-limiting example, an efficacy profile may indicate that a user is a very slow metabolizer of a first prescriptive therapy and as such, is at greater risk of developing toxicity and experiencing side effects. Computing device 104 identifies a second prescriptive therapy containing a second efficacy profile and recommends the second prescriptive therapy as a function of the second efficacy profile. For instance and without limitation, computing device 104 determines a first efficacy profile of a first prescriptive therapy such as fluvastatin that indicates a user is a very poor metabolizer of fluvastatin. In such an instance, computing device 104 identifies a second prescriptive therapy such as rosuvastatin, that contains a second efficacy profile indicating the user is a normal metabolizer of the rosuvastatin. In such an instance, computing device 104 recommends the second prescriptive therapy of rosuvastatin based on its efficacy profile. Computing device 104 may identify a second prescriptive therapy containing a second efficacy profile and recommend the second prescriptive therapy when the second prescriptive therapy is related to the first prescriptive therapy. A second prescriptive therapy is related to a first prescriptive therapy when the prescriptive therapies belong to the same drug class or are used to treat the same medical condition and/or diagnosis, as described above in more detail in reference to FIG. 1. Computing device 104 identifies a first prescriptive therapy companion, including any of the prescriptive therapy companions as described above. Computing device 104 locates a second prescriptive therapy as a function of a first prescriptive therapy companion and recommends administration of the first prescriptive therapy and the second prescriptive therapy.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 8:
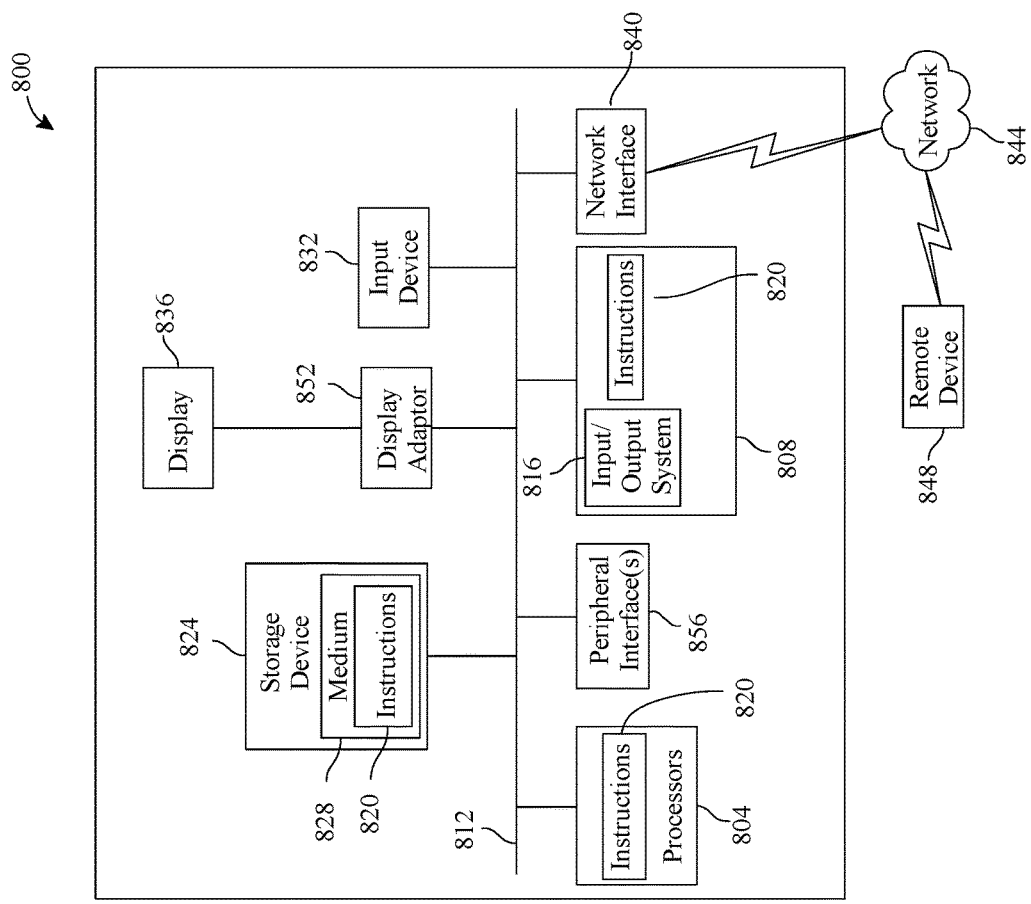
FIG. 8 is a block diagram of a computing system that can be used to implement any one or more of the methodologies disclosed herein and any one or more portions thereof.

FIG. 8 shows a diagrammatic representation of one embodiment of a computing device in the exemplary form of a computer system 800 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 800 includes a processor 804 and a memory 808 that communicate with each other, and with other components, via a bus 812. Bus 812 may include any of several types of bus structures including, but not limited to, a memory bus, a memory controller, a peripheral bus, a local bus, and any combinations thereof, using any of a variety of bus architectures.

Memory 808 may include various components (e.g., machine-readable media) including, but not limited to, a random access memory component, a read only component, and any combinations thereof. In one example, a basic input/output system 816 (BIOS), including basic routines that help to transfer information between elements within computer system 800, such as during start-up, may be stored in memory 808. Memory 808 may also include (e.g., stored on one or more machine-readable media) instructions (e.g., software) 820 embodying any one or more of the aspects and/or methodologies of the present disclosure. In another example, memory 808 may further include any number of program modules including, but not limited to, an operating system, one or more application programs, other program modules, program data, and any combinations thereof.

Computer system 800 may also include a storage device 824. Examples of a storage device (e.g., storage device 824) include, but are not limited to, a hard disk drive, a magnetic disk drive, an optical disc drive in combination with an optical medium, a solid-state memory device, and any combinations thereof. Storage device 824 may be connected to bus 812 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 824 (or one or more components thereof) may be removably interfaced with computer system 800 (e.g., via an external port connector (not shown)). Particularly, storage device 824 and an associated machine-readable medium 828 may provide nonvolatile and/or volatile storage of machine-readable instructions, data structures, program modules, and/or other data for computer system 800. In one example, software 820 may reside, completely or partially, within machine-readable medium 828. In another example, software 820 may reside, completely or partially, within processor 804.

Computer system 800 may also include an input device 832. In one example, a user of computer system 800 may enter commands and/or other information into computer system 800 via input device 832. Examples of an input device 832 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 832 may be interfaced to bus 812 via any of a variety of interfaces (not shown) including, but not limited to, a serial interface, a parallel interface, a game port, a USB interface, a FIREWIRE interface, a direct interface to bus 812, and any combinations thereof. Input device 832 may include a touch screen interface that may be a part of or separate from display 836, discussed further below. Input device 832 may be utilized as a user selection device for selecting one or more graphical representations in a graphical interface as described above.

A user may also input commands and/or other information to computer system 800 via storage device 824 (e.g., a removable disk drive, a flash drive, etc.) and/or network interface device 840. A network interface device, such as network interface device 840, may be utilized for connecting computer system 800 to one or more of a variety of networks, such as network 844, and one or more remote device 144 848 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 844, may employ a wired and/or a wireless mode of communication. In general, any network topology may be used. Information (e.g., data, software 820, etc.) may be communicated to and/or from computer system 800 via network interface device 840.

Computer system 800 may further include a video display adapter 852 for communicating a displayable image to a display device, such as display device 836. Examples of a display device include, but are not limited to, a liquid crystal display (LCD), a cathode ray tube (CRT), a plasma display, a light emitting diode (LED) display, and any combinations thereof. Display adapter 852 and display device 836 may be utilized in combination with processor 804 to provide graphical representations of aspects of the present disclosure. In addition to a display device, computer system 800 may include one or more other peripheral output devices including, but not limited to, an audio speaker, a printer, and any combinations thereof. Such peripheral output devices may be connected to bus 812 via a peripheral interface 856. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for informed selection of prescriptive therapies, the system comprising a computing device, the computing device configured to:
   retrieve an element of user genetic data;
   determine a prescriptive therapy label as a function of the user genetic data,
      wherein determining the prescriptive therapy label comprises utilizing a prescriptive label machine-learning model that receives the user genetic data as an input and outputs the prescriptive therapy label;
   determine a prescriptive therapy instruction set including a first prescriptive therapy as a function of the prescriptive therapy label, where determining further comprises:
      generating a prescriptive machine-learning process, wherein the prescriptive machine-learning process comprises a prescriptive machine-learning model, wherein the prescriptive machine-learning model is trained, iteratively, using prescriptive training data, wherein the prescriptive training data contains a plurality of data entries containing a prescriptive therapy label element correlated to a prescriptive therapy instruction set element by a proximity within the plurality of data entries;
      inputting the prescriptive therapy label, output from the prescriptive machine-learning model, into the prescriptive machine-learning process; and
      generating a prescriptive therapy instruction set as a function of the prescriptive therapy label using the prescriptive machine-learning process, wherein the prescriptive therapy instruction set comprises a monitoring recommendation, and wherein the monitoring recommendation comprises measuring one or more biological extractions of the user over a predetermined time interval; and
   wherein the system further comprises a graphical user interface (GUI), the GUI configured to display one or more selectable photographs associated with one or more prescriptive therapies, respectively.

2. The system of claim 1, wherein the prescriptive therapy label comprises a negative therapy response.

3. The system of claim 1, wherein the computing device is further configured to:
   retrieve from a user profile database, a user specific indication for the first prescriptive therapy; and
   calculate the prescriptive therapy instruction set using the user specific indication.

4. The system of claim 1, wherein the prescriptive machine-learning process comprises a supervised machine-learning process.

5. The system of claim 1, wherein the computing device is further configured to:
   recommend a user to not consume the first prescriptive therapy; and
   recommend a second prescriptive therapy.

6. The system of claim 1, wherein the computing device is further configured to recommend a dose adjustment to the first prescriptive therapy as a function of the prescriptive machine-learning process.

7. The system of claim 1, wherein the computing device is further configured to:
   determine a first efficacy profile of the first prescriptive therapy;
   identify a second prescriptive therapy containing a second efficacy profile; and
   recommend the second prescriptive therapy as a function of the second efficacy profile.

8. The system of claim 7, wherein the first prescriptive therapy is related to the second prescriptive therapy.

9. The system of claim 1, wherein the computing device is further configured to:
   identify a first prescriptive therapy companion;
   locate a second prescriptive therapy as a function of the first prescriptive therapy companion; and
   recommend administration of the first prescriptive therapy and the second prescriptive therapy.

10. The system of claim 1, wherein the predetermined time interval comprises one month.

11. A method of informed selection of prescriptive therapies, the method comprising:

retrieving, by a computing device, an element of user genetic data;

determining, by a computing device, a prescriptive therapy label as a function of the user genetic data, wherein determining the prescriptive therapy label comprises utilizing a prescriptive label machine-learning model that receives the user genetic data as an input and outputs the prescriptive therapy label;

determining by the computing device, a prescriptive therapy instruction set including a first prescriptive therapy as a function of the prescriptive therapy label, wherein determining further comprises:

generating a prescriptive machine-learning process, wherein the prescriptive machine-learning process comprises a prescriptive machine-learning model, wherein the prescriptive machine-learning model is trained, iteratively, using prescriptive training data, wherein the prescriptive training data contains a plurality of data entries containing a prescriptive therapy label element correlated to a prescriptive therapy instruction set element by a proximity within the plurality of data entries;

inputting the prescriptive therapy label, output from the prescriptive machine-learning model, into the prescriptive machine-learning process; and generating, by the computing device, a prescriptive therapy instruction set as a function of the prescriptive therapy label using the prescriptive machine-learning process, wherein the prescriptive therapy instruction set comprises a monitoring recommendation, and wherein the monitoring recommendation comprises measuring one or more biological extractions of the user over a predetermined time interval; and displaying, by a graphical user interface (GUI), one or more selectable photographs associated with one or more prescriptive therapies, respectively.

12. The method of claim 11, wherein the prescriptive therapy label comprises a negative therapy response.

13. The method of claim 11, wherein generating the prescriptive therapy instruction set further comprises:

retrieving from a user profile database, a user specific indication for the first prescriptive therapy; and calculating the prescriptive therapy instruction set using the user specific indication.

14. The method of claim 11, wherein the prescriptive machine-learning process comprises a supervised machine-learning process.

15. The method of claim 11, wherein recommending the prescriptive therapy instruction set further comprises:

recommending a user to not consume the first prescriptive therapy; and recommending a second prescriptive therapy.

16. The method of claim 11, wherein recommending the prescriptive therapy instruction set further comprises recommending a dose adjustment to the first prescriptive therapy as a function of the prescriptive machine-learning process.

17. The method of claim 11, wherein recommending the prescriptive therapy instruction set further comprises:

determining a first efficacy profile of the first prescriptive therapy;

identifying a second prescriptive therapy containing a second efficacy profile; and recommending the second prescriptive therapy as a function of the second efficacy profile.

18. The method of claim 17, wherein the first prescriptive therapy is related to the second prescriptive therapy.

19. The method of claim 11, wherein recommending the prescriptive therapy instruction set further comprises:

identifying a first prescriptive therapy companion;

locating a second prescriptive therapy as a function of the first prescriptive therapy companion; and recommending administration of the first prescriptive therapy and the second prescriptive therapy.

20. The method of claim 11, wherein the predetermined time interval comprises one month.

* * * * *